United States Patent
Rajagopalan et al.

(10) Patent No.: US 7,674,902 B2
(45) Date of Patent: Mar. 9, 2010

(54) LUMINESCENT METAL COMPLEXES FOR MONITORING RENAL FUNCTION

(75) Inventors: Raghavan Rajagopalan, Solon, OH (US); Richard B. Dorshow, St. Louis, MO (US); Dennis A. Moore, St. Louis, MO (US)

(73) Assignee: Mallinckrodt Inc., St. Louis, MO (US)

( * ) Notice: Subject to any disclaimer, the term of this patent is extended or adjusted under 35 U.S.C. 154(b) by 195 days.

(21) Appl. No.: 11/572,920

(22) PCT Filed: Aug. 3, 2005

(86) PCT No.: PCT/US2005/027486

§ 371 (c)(1),
(2), (4) Date: Jan. 30, 2007

(87) PCT Pub. No.: WO2006/026038

PCT Pub. Date: Mar. 9, 2006

(65) Prior Publication Data

US 2008/0299038 A1    Dec. 4, 2008

Related U.S. Application Data

(60) Provisional application No. 60/604,573, filed on Aug. 26, 2004.

(51) Int. Cl.
   *C07D 471/00*    (2006.01)
(52) U.S. Cl. .................................................. 544/349
(58) Field of Classification Search ................. 562/400; 544/349
   See application file for complete search history.

(56) References Cited

U.S. PATENT DOCUMENTS

| | | | |
|---|---|---|---|
| 5,334,729 A | | 8/1994 | Mease et al. |
| 5,453,264 A | * | 9/1995 | Mori et al. ............... 424/9.364 |
| 5,463,030 A | * | 10/1995 | Subramanian et al. ........ 534/16 |
| 5,859,214 A | * | 1/1999 | Gries et al. .................... 534/16 |
| 6,040,432 A | | 3/2000 | Krause et al. |
| 6,277,841 B1 | | 8/2001 | Rajagopalan et al. |
| 6,440,389 B1 | | 8/2002 | Rabito |
| 2002/0072625 A1 | | 6/2002 | Johnson |
| 2003/0099598 A1 | | 5/2003 | Kiefer et al. |

FOREIGN PATENT DOCUMENTS

| EP | 0451824 | 10/1991 |
|---|---|---|
| EP | 1092723 | 4/2001 |

OTHER PUBLICATIONS

Ownby et al., 1975, CAS: 83:158823.*
Bai et al., 1997, CAS: 127: 122970.*
Wei et al., 1999, CAS: 130: 104329.*

Ozaki et al., Sensitization of Europhium(III) Luminescence by DTPA Derivatives, Chemistry Letters, Chemical Society of Japan, 2000, vol. 4, pp. 312-313, XP001076648.

Nally, Jr., Joseph V., Acute renal failure in hospitalized patients, Cleveland Clinic Journal of Medicine, 2002, 69(7), pp. 569-574.

Mikola, H. et al., Syntheses and Properties of Luminescent Lanthanide Chelate Labels and Labeled Haptenic . . . , Bioconjugate chemistry, 1995, 6(3), pp. 235-241.

Gunnlaugsson et al., Luminescent europium tetraazamacrocyclic complexes with wide range pH sensitivity, 1998, Chem. Commun., pp. 511-512.

Chen et al., Thiol-Reactive Luminescent Chelates of Terbium and Europhium, Bioconjugate Chem., 1999, 10, pp. 311-315.

Nosco et al., Chemistry of technetium radiopharmaceuticals 1: Chemistry behind the development of technetium-99m compounds to determine kidney function, Reprinted from Coordination Chemistry Reviews an International Journal, Coordination Chemistry Reviews 184, 1999, pp. 91-123.

Griffin, et al., Simple, high yielding synthesis of trifunctional fluorescent lanthanide Chelates, Tetrahedron Letters 42, 2001, pp. 3823-3825.

Abusaleh et al., Excitation and De-Excitation Processes In Lanthanide Chelates Bearing Aromatic Sidechains, Photochemistry and Photobiology, 1984, vol. 39, No. 6, pp. 763-769.

International Search Report, dated Nov. 24, 2005, mailed Jan. 12, 2005.

Anelli et al., "$_L$-Glutamic id and $_L$-Lysine as Useful Building Blocks for the Preparation of Bifunctional DTPA-like Ligands", Bioconjugate Chem., 1999, 10, pp. 137-140.

Rapoport et al., "Preparation of Functionalized, Conformationally Constrained DTPA analogues from $_L$- or $_D$-Serine and *trans*-4-Hydroxy-$_L$-proline. Hydroxymethyl Substituents on the Central Acetic Acid and on the Backbone", J. Org. Chem., 2000, 65, pp. 4047-4057.

(Continued)

*Primary Examiner*—Rei-tsang Shiao
(74) *Attorney, Agent, or Firm*—Thompson Hine LLP

(57) ABSTRACT

Some embodiments of the present invention may be said to be directed to metal complexes of Formula I, wherein at least one of $X^1$, $X^2$, $X^3$, $R^1$, $R^2$, $R^3$, $R^4$ and $R^5$ is what may be characterized as an antenna capable of providing (e.g., absorbing and/or emitting) an appropriate electromagnetic signal. Some embodiments of the present invention are directed to ligands corresponding to metal complexes of Formula I. Some embodiments of the invention are directed to methods of determining renal function using at least one metal complex of Formula I.

(I)

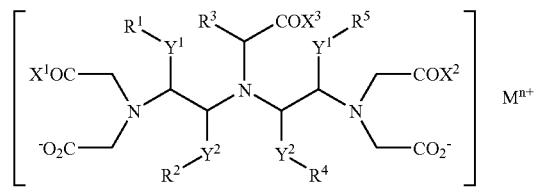

17 Claims, 14 Drawing Sheets

OTHER PUBLICATIONS

Gouin et al., "Synthesis of a new chelating agent derived from phenylenediamine for application in radioimmunotherapy", Tetrahedron Letters 43, 2002, pp. 3003-3005.

Chong et al., "Synthesis of DTPA Analogues Derived from Piperidine and Azepane: Potential Contrast Enhancement Agents for Magnetic Resonance Imaging", J. Org. Chem., 2001, 66, pp. 7745-7750.

Rapoport et al., "Synthesis of Enantiomerically Pure Diehylenetriaminepentaacetic Acid Analogues. $_L$-Phenylalanine as the Educt for Substitution at the Central Acetic Acid", J. Org. Chem., 1993, 58, pp. 1151-1158.

European Office Action dated Mar. 16, 2009.

Response to European Office Action (mailed May 26, 2009); with of Declaration of William L. Neumann, PhD.

* cited by examiner

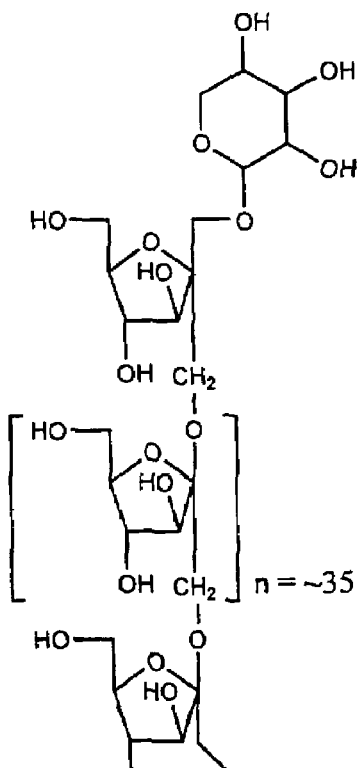
Inulin (1)
MW: ~5,000
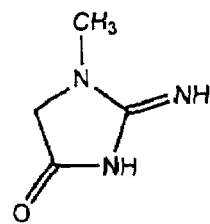
Creatinine (2)
MW: 113
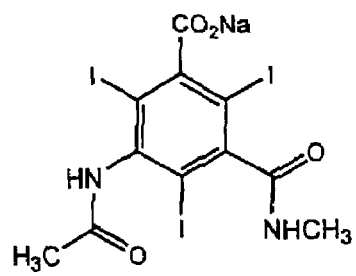
Iothalamate (3)
MW: 636
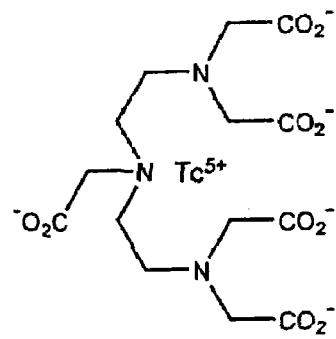
99mTc-DTPA (4)
MW: 487
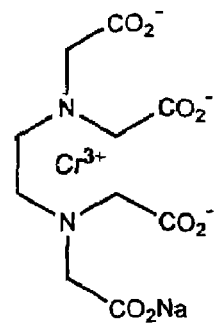
51Cr-EDTA (5)
MW: 362
Fig. 1

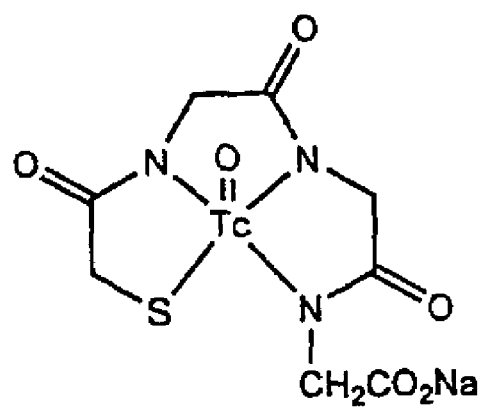 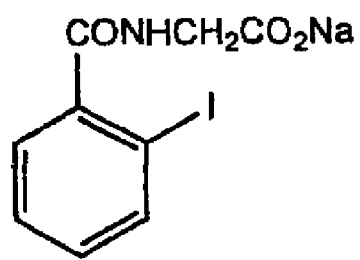
99mTc-MAG3 (6)
MW: 364
o-Iodohippurate (7)
MW: 327
Fig. 2

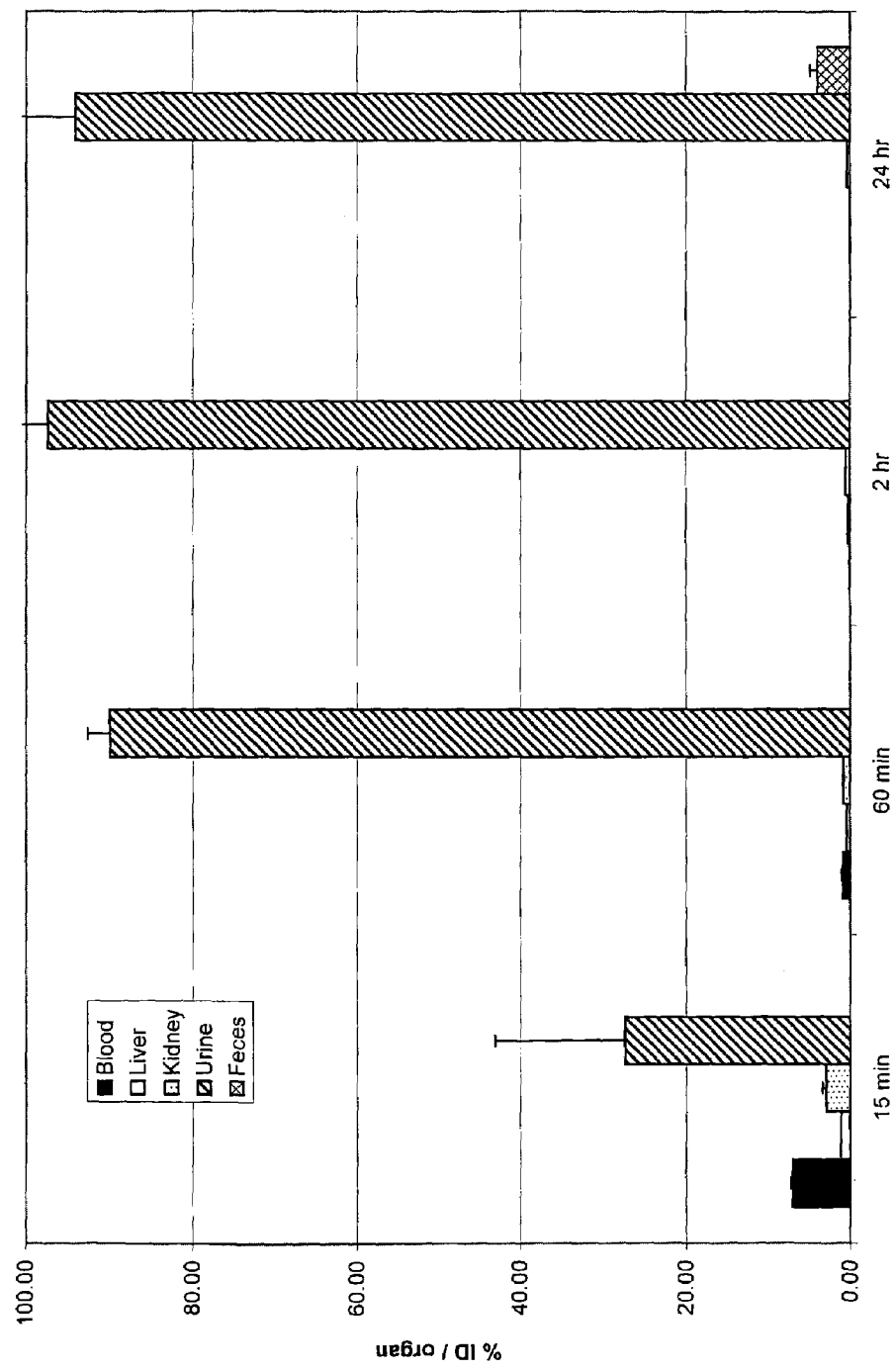

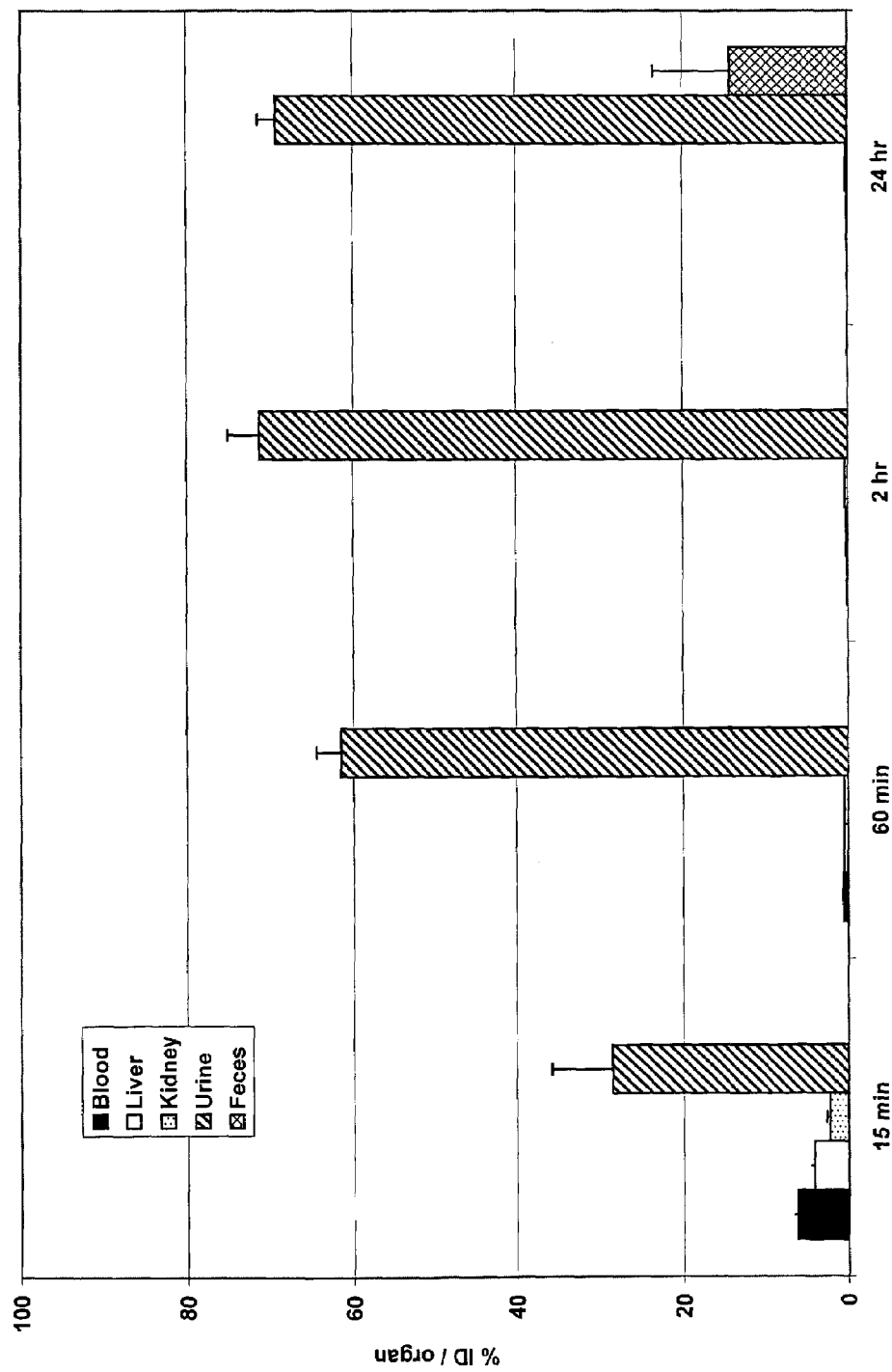

LUMINESCENT METAL COMPLEXES FOR MONITORING RENAL FUNCTION

FIELD OF THE INVENTION

The present invention relates to fluorescent diethylenetriaminepentaacetate (DTPA) metal complexes, corresponding DTPA ligands, and methods of monitoring renal function using such metal complexes.

BACKGROUND

It is to be noted that throughout this application, various publications are referenced by Arabic numerals in brackets. Full citation corresponding to each reference number is listed at the end of the specification. The disclosures of these publications are herein incorporated by reference in their entirety in order to describe fully and clearly the state of the art to which this invention pertains.

Acute renal failure (ARF) is a common ailment in patients admitted to the general medical-surgical hospitals. Furthermore, approximately half of the patients who develop ARF die, and survivors face marked increases in morbidity and prolonged hospitalization [1]. Early diagnosis is critical because renal failure is often asymptomatic, and it requires careful tracking of renal function markers in the blood. Dynamic monitoring of renal functions of patients at the bedside is highly desirable in order to minimize the risk of acute renal failure brought about by various clinical, physiological, and pathological conditions [2-6]. It is particularly important in the case of critically ill or injured patients because a large percentage of these patients face the risk of multiple organ failure (MOF) resulting in death [7, 8]. MOF is a sequential failure of lung, liver, and kidneys and is incited by one or more severe causes such as acute lung injury (ALI), adult respiratory distress syndrome (ARDS), hypermetabolism, hypotension, persistent inflammatory focus, or sepsis syndrome. The common histological features of hypotension and shock leading to MOF include tissue necrosis, vascular congestion, interstitial and cellular edema, hemorrhage, and microthrombi. These changes affect the lung, liver, kidneys, intestine, adrenal glands, brain, and pancreas in descending order of frequency [9]. The transition from early stages of trauma to clinical MOF is marked by the extent of liver and renal failure and a change in mortality risk from about 30% to about 50% [10].

Currently, the renal function is determined commonly by crude measurements such as urine output and plasma creatinine levels [11-13]. These values are frequently misleading because the values are affected by age, state of hydration, renal perfusion, muscle mass, dietary intake, and many other clinical and anthropometric variables. In addition, a single value obtained several hours after sampling is difficult to correlate with other important physiologic events such as blood pressure, cardiac output, state of hydration and other specific clinical events (e.g., hemorrhage, bacteremia, ventilator settings and others). An approximation of glomerular filtration rate (GFR) can be made via a 24 hour urine collection, but this process requires 24 hours to collect, several more hours to analyze, and a meticulous bedside collection technique. Unfortunately, detecting a patient's GFR by this time may be too late to treat the patient and have any hope of saving the kidney. New or repeat data are equally cumbersome to obtain. Occasionally, changes in serum creatinine must be further adjusted based on the values for urinary electrolytes, osmolality, and derived calculations such as the "renal failure index" or the "fractional excretion of sodium." These require additional samples of serum collected contemporaneously with urine samples and, after a delay, precise calculations. Frequently, dosing of medication is adjusted for renal function and thus can be equally as inaccurate, equally delayed, and as difficult to reassess as the values upon which they are based. Finally, clinical decisions in the critically ill population are often equally as important in their timing as they are in their accuracy. Thus, there is a need to develop improved devices and methods for measuring GFR using non-ionizing radiation. The availability of a real-time, accurate, repeatable measure of renal excretion rate using exogenous markers under specific yet changing circumstances would represent a substantial improvement over any currently available or widely practiced method. Moreover, since such a method would depend solely on the renal elimination of the exogenous chemical entity, the measurement would be absolute and requires no subjective interpretation based on age, muscle mass, blood pressure, etc. In fact, if such a method were developed, it would represent the nature of renal function in the particular patient, under particular circumstances, at a precise moment in time.

Hydrophilic, anionic substances are generally recognized to be excreted by the kidneys [14]. Renal clearance occurs via two pathways, glomerular filtration and tubular secretion; the latter requires an active transport process, and hence, the substances clearing via this pathway are expected to possess very specific properties with respect to size, charge, and lipophilicity. It is widely accepted that the level of GFR represents the best overall measure of kidney function in the state of health or illness [15]. Fortunately, however, most of the substances that pass through the kidneys are filtered through the glomerulus. The structures of typical exogenous renal agents are shown in FIGS. 1 and 2. Substances clearing by glomerular filtration (hereinafter referred to as 'GFR agents') comprise inulin (1), creatinine (2), iothalamate (3) [16-18], $^{99m}$Tc-DTPA (4), and $^{51}$Cr-EDTA (5), those undergoing clearance by tubular secretion include $^{99m}$Tc-MAG3 (6) and o-iodohippuran (7) [16, 19, 20]. Among these, inulin is regarded as the "gold standard" for GFR measurement. All the compounds shown in FIGS. 1 and 2, except creatinine, require radioisotopes for detection.

As would be evident to one skilled in the art, cursory inspection of structures 1-7 provides no insight to ascertain the subtle factors responsible for directing the molecule to clear via a particular renal pathway. Clearly, gross physicochemical features such as charge, molecular weight, or lipophilicity are inadequate in even explaining the mode of clearance. Inulin (1, MW~5000) and creatinine (2, MW 113) are both filtered through the glomerulus. On the other hand, the anionic chromium complex 5 (MW 362) and technetium complex 6 (MW 364) are cleared by different pathways. Structure-activity relationship (SAR) data on this very limited set of compounds is insufficient to ascertain the subtle differences between the two clearance pathways. Therefore, at the time of instant invention, prior art publications could not be relied upon to provide sufficient teaching or motivation for rational design of novel GFR agents. Thus, each new compound must be tested and compared against a known GFR agent, such as $^{99m}$Tc-DTPA (4) or inulin (1), to confirm the clearance pathway.

As mentioned before, most of the currently known exogenous renal agents are radioactive. Currently, no reliable, continuous, repeatable bedside method for the assessment of specific renal function using non-radioactive exogenous GFR agent is commercially available. Among the non-radioactive methods, fluorescence measurement offers the greatest sensitivity. In principle, there are two general approaches for designing fluorescent GFR agents. The first approach involves enhancing the fluorescence of known renal agents (e.g. lanthanide or transition metal complexes) that are intrinsically poor emitters; and the second one involves transforming highly fluorescent conventional dyes, which are intrinsically lipophilic, into hydrophilic, anionic species to force them to clear via the kidneys. The present invention focuses on the former approach. Metal complexes of DTPA, DTPA-monoamides, DTPA-bisamides, and DTPA substituted at the ethylene portion of the ligand, have been used extensively in biomedical applications, and have been shown to clear through the kidneys. Work described in [21, 22, and 23] have independently suggested the use of luminescent metal complexes derived from polyaminocarboxylate ligands for measuring renal clearance.

The method of enhancing the fluorescence through intramolecular energy transfer process is well established [24], and has been applied to boost the fluorescence of metal ion through ligand-metal energy transfer [25-28]. The method essentially involves designing metal complexes containing an "antenna". As used herein, an antenna is a moiety that has high photon capture cross section placed at an optimal distance (referred to as 'Foster' distance) from the metal ion wherein the moiety has a large surface area and a polarizable electron cloud. The distance between the antenna and the metal ion ranges from about 2-20 Å, preferably, from about 3-10 Å.

Novel fluorescent DTPA complexes for use in improved methods for providing data related to organ functioning are described below. These complexes may be said by some to be capable of real-time, accurate, repeatable measure of renal excretion rate.

SUMMARY

A first aspect of the invention is directed to DTPA complexes of Formula I below. With regard to this first aspect, M is generally a metal ion whose absorption and emission occur in the visible and/or NIR region, and n is at least 1. At least one of the substituents, $X^1$ to $X^3$ and $R^1$ to $R^5$, in Formula I is generally an antenna. The other remaining R and/or X groups may optionally be introduced to optimize biological and/or physicochemical properties of the metal complex. Each of $Y^1$ and $Y^2$ is independently a single bond or a spacer group that connects the antenna or other substituent group to the DTPA.

In a second aspect of the invention, DTPA ligands corresponding to complexes of Formula I are provided. The DTPA ligands of this second aspect are believed to be useful for, among others things, preparing metal complexes, such as metal complexes of Formula I.

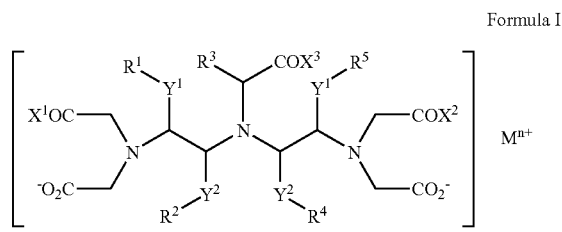

Formula I

Yet a third aspect of the invention is directed to methods of determining renal function using at least one metal complex, such as one or more metal complexes of Formula I. With regard to this third aspect, an effective amount of a metal complex(es) (e.g., a metal complex of Formula I) capable of absorbing and emitting electromagnetic radiation at different wavelengths is administered into the body of a patient (e.g., a mammal such as a human subject or other animal subject). A signal emanating from a body portion in the patient's body is detected (e.g., at one or more times or continuously in real-time). This signal results from the metal complex(es) not yet removed from the body during the detection. Renal function is determined based on the detection of the signal.

BRIEF DESCRIPTION OF THE DRAWINGS

FIG. 1: Structures of molecules clearing via glomerular filtration.

FIG. 2: Structures of molecules clearing via tubular secretion.

FIG. 13: Bar graph of normal rat biodistribution of $^{111}$In-DTPA-mono(pyrazinylamino)ethylamide complex.

FIG. 14: Bar graph of normal rat biodistribution of $^{111}$In-DTPA-mono(quinoxanylamino)ethylamide complex.

DETAILED DESCRIPTION

Figure 3:
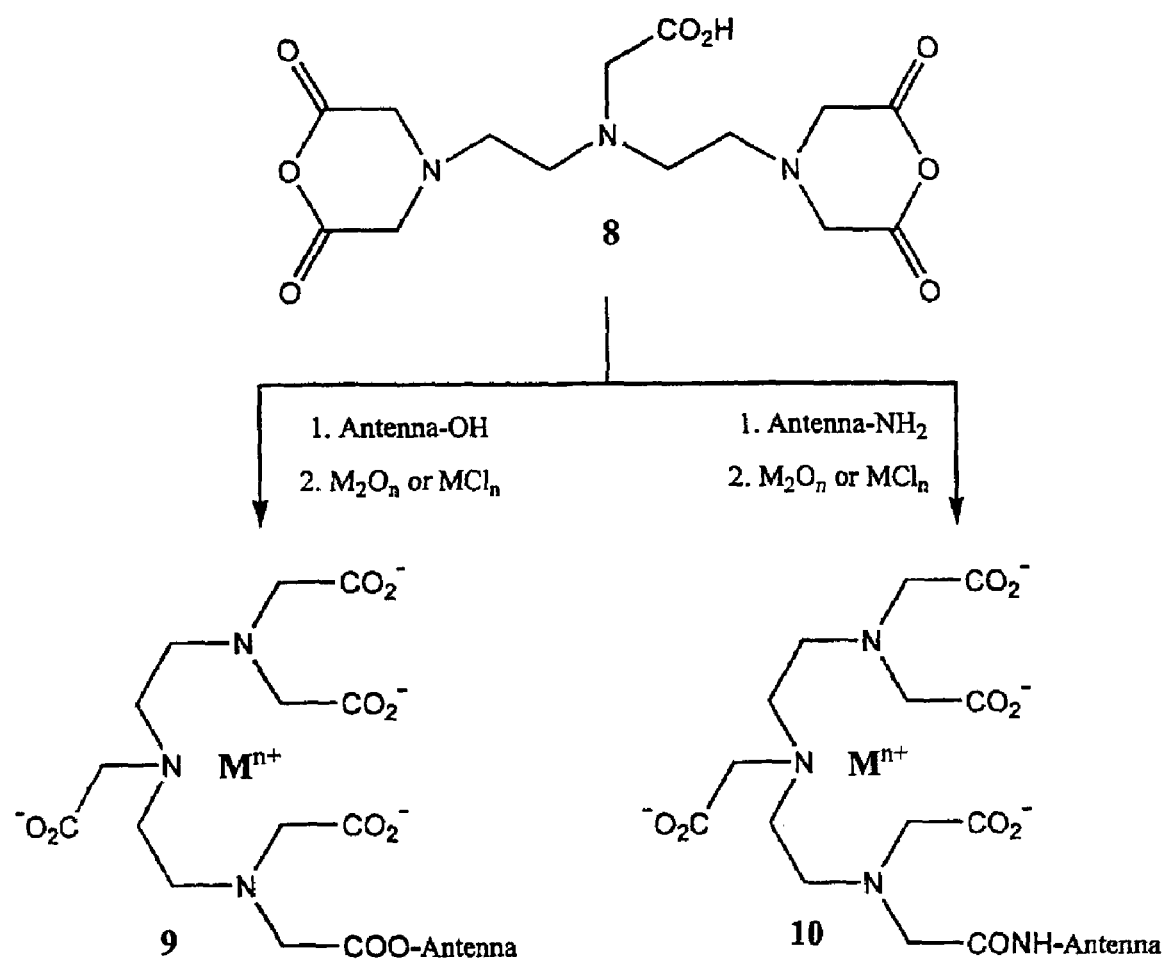
FIG. 3: Attachment of the antenna at the carboxyl position in DTPA.

Exemplary embodiments of the present invention include renal function monitoring compositions of Formula I. With regard to these embodiments, M is a metal ion whose absorption and emission occur in the visible and/or NIR region, and n varies from 1 to 5. Suitable metal ions, M, include, but are not limited to, the lanthanide series of elements such as Eu, Tb, Dy and Sm, and the transition metals such as Rh, Re, Ru, and Cr, and Group IIIb metals such as Ga and In, and the like. For instance, in some embodiments, M is chosen from Eu, Tb, Dy, Sm, Rh, Re, Ru, Cr and In.

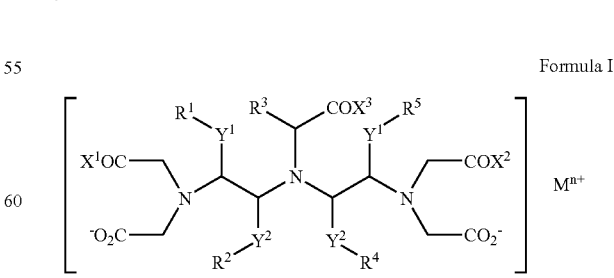

Formula I

As a further description of the exemplary embodiments, each of $X^1$, $X^2$ and $X^3$ is independently an antenna, $-O^-$, $-NH(CH_2)_aOH$, $-NH(CH_2)_aCO_2H$, $-NH(CH_2)_aSO_3^-$, —NH(CH$_2$)$_a$OSO$_3^-$, —NH(CH$_2$)$_a$NHSO$_3$, —O(CH$_2$)$_a$SO$_3^-$, —O(CH$_2$)$_a$OSO$_3^-$, —O(CH$_2$)$_a$NHSO$_3^-$, —NH(CH$_2$)$_a$PO$_3$H$^-$, —NH(CH$_2$)$_a$PO$_3^=$, —NH(CH$_2$)$_a$OPO$_3$H$^-$, —NH(CH$_2$)$_a$OPO$_3^=$, —NH(CH$_2$)$_a$NHOPO$_3$H$^-$, —NH(CH$_2$)$_a$NHPO$_3^-$, —O(CH$_2$)$_a$PO$_3$H$^-$, —O(CH$_2$)$_a$PO$_3^-$, —O(CH$_2$)$_a$OPO$_3$H$^-$, —O(CH$_2$)$_a$OPO$_3$H$^=$, —O(CH$_2$)$_a$NHPO$_3$H$^-$, and —O(CH$_2$)$_a$NHPO$_3$H$^=$; a ranges from 1 to 6. Each of R$^1$ to R$^5$ is independently an antenna, hydrogen, C1-C10 alkyl, C1-C10 hydroxyalkyl, C1-C10 polyhydroxyalkyl, carboxyl, C1-C10 carboxyalkyl, C1-C10 alkoxyalkyl, —(CH$_2$)$_b$SO$_3^-$, —(CH$_2$)$_b$OSO$_3^-$, —(CH$_2$)$_b$NHSO$_3^-$, —(CH$_2$)$_b$CO$_2$(CH$_2$)$_c$SO$_3^-$, —(CH$_2$)$_b$OCO(CH$_2$)$_c$SO$_3^-$, —(CH$_2$)$_b$CONH(CH$_2$)$_c$SO$_3^-$, —(CH$_2$)$_b$NHCO(CH$_2$)$_c$SO$_3^-$, —(CH$_2$)$_b$NHCONH(CH$_2$)$_c$SO$_3^-$, —(CH$_2$)$_b$NHCSNH(CH$_2$)$_c$SO$_3^-$, —(CH$_2$)$_b$OCONH(CH$_2$)$_c$SO$_3^-$, —(CH$_2$)$_b$PO$_3$H$^-$, —(CH$_2$)$_b$PO$_3^=$, —(CH$_2$)$_b$OPO$_3$H$^-$, —(CH$_2$)$_b$OPO$_3^=$, —(CH$_2$)$_b$NHPO$_3$H$^-$, —(CH$_2$)$_b$NHPO$_3^=$, —(CH$_2$)$_b$CO$_2$(CH$_2$)$_c$PO$_3$H$^-$, —(CH$_2$)$_b$CO$_2$(CH$_2$)$_c$PO$_3^=$, —(CH$_2$)$_b$OCO(CH$_2$)$_c$PO$_3$H$^-$, —(CH$_2$)$_b$OCO(CH$_2$)$_c$PO$_3^=$, —(CH$_2$)$_b$CONH(CH$_2$)$_b$PO$_3$H$^-$, —(CH$_2$)$_b$CONH(CH$_2$)$_c$PO$_3$H$^-$, —(CH$_2$)$_b$NHCO(CH$_2$)$_c$PO$_3^=$, —(CH$_2$)$_b$NHCO(CH$_2$)$_c$PO$_3$H$^-$, —(CH$_2$)$_b$NHCONH(CH$_2$)$_c$PO$_3$H$^=$, —(CH$_2$)$_b$NHCSNH(CH$_2$)$_c$PO$_3$H$^-$, —CH$_2$)$_b$NHCSNH(CH$_2$)$_c$PO$_3^=$, —(CH$_2$)$_b$OCONH(CH$_2$)$_c$PO$_3$H$^-$, and —(CH$_2$)$_b$OCONH(CH$_2$)$_c$PO$_3^=$. The constituents, b and c, range from 1 to 6, and at least one of X$^1$, X$^2$, X$^3$ and R$^1$ to R$^5$ is an antenna.

Each of Y$^1$ and Y$^2$ is independently a single bond or a spacer group, such as —(CH$_2$)$_m$—, —(CH$_2$)$_m$O—, —(CH$_2$)$_m$OCO—, —(CH$_2$)$_m$CO$_2$—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$NHCSNH—, —(CH$_2$)$_m$OSO$_2$—, (CH$_2$)$_m$OSO$_3$—, (CH$_2$)$_m$SO$_2$—, —(CH$_2$)$_m$NHSO$_2$—, and —(CH$_2$)$_m$SO$_2$NH—. In some embodiments, m varies from 1 to 10, while in other embodiments, m varies from 1 to 6.

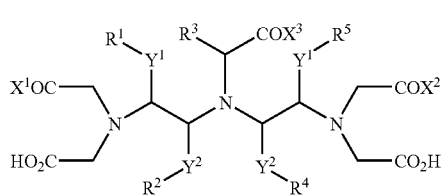

Formula II

Some embodiments of the invention include ligands corresponding to the metal complexes of formula I. Such embodiments are represented by formula II above. X$^1$ to X$^3$, Y$^1$ and Y$^2$, and R$^1$ to R$^5$ in formula II correspond to those same substituents as defined in formula I. For substituents X$^1$ to X$^3$ and R$^1$ to R$^5$ that are shown in their anion form, it is noted that those substituents can optionally be in the corresponding neutral form (e.g., —O$^-$ can be either —O$^-$ or —OH).

Regarding the exemplary embodiments of the compositions formula I above, if R$^1$ to R$^5$ are hydrogens, and if M$^{n+}$ is a lanthanide ion, then X$^1$ to X$^3$ are not derived from aniline, benzylamine, 2-aminomethyl-pyridine, 1-amino-naphthalene, 2-aminonaphthalene, 7-amino-4-methylcoumarin, 4-aminosalicylic acid, 2-(2-aminoethyl)aminopyrazine, 2-(2-aminoethyl)-aminopyrazine, 2-(2-aminoethyl)amino-quinoxaline-2-carboxylic acid, or 2-(2-aminoethyl)amino-quinoxaline-2-carboxamide. In addition, if X$^1$ to X$^3$ are —O$^-$, and if M$^{n+}$ is a lanthanide ion, then R$^1$ to R$^5$ are not phenyl or benzyl.

Regarding the ligands of formula II above, if R$^1$ to R$^5$ are hydrogens, then X$^1$ to X$^3$ are not derived from aniline, benzylamine, 2-aminomethyl-pyridine, 1-aminonaphthalene, 2-amino-naphthalene, 7-amino-4-methylcoumarin, 4-aminosalicylic acid, 2-(2-aminoethyl)aminopyrazine, 2-(2-aminoethyl)-aminopyrazine, 2-(2-aminoethyl)aminoquinoxaline-2-carboxylic acid, or 2-(2-aminoethyl)-aminoquinoxaline-2-carboxamide. In addition, if X$^1$ to X$^3$ are —O$^-$, then R$^1$ to R$^5$ are not phenyl or benzyl.

An "antenna" refers to a group whose absorption and emission preferably occur in the visible and/or NIR region. Suitable antennae are typically aromatic or heteroaromatic chromophores that are derived from unsubstituted or substituted aromatic or heteroaromatic compounds. The aromatic or heteroaromatic compound can be represented by the formula Ar-Z, where Z is a linker group, and the antenna can be represented by the formula Ar-Z'-. The base aromatic or heteroaromatic ring structure preferably is monocyclic or bicyclic and contains 5 to 10 carbon atoms. The aromatic or heteroaromatic ring structure can optionally contain substituent groups other than Z (e.g., alkyl groups such as methyl). An example of such a substituted Ar-Z compound is 7-amino-4-methylcoumarin. The aromatic or heteroaromatic ring structure can also optionally be substituted with one or more hydrophilic groups, W. Suitable W groups include, but are not limited to, —COOH, —NH$_2$, —OH, —SO$_3$H, —PO$_3$H$_2$, and the like. For the development of renal agents of some embodiments, the aromatic or heteroaromatic ring structure is substituted with at least one W group.

Suitable antennae include, but are not limited to, Ar-Z'-groups derived from substituted or unsubstituted benzene, pyridine, pyrazine, pyrimidine, pyridazine, naphthalene, quinoline, quinoxaline (also known as 2,3-benzopyrazine or quinazine), coumarin, benzofuran, isobenzofuran, indole, isoindole, benzimidazole, benzothiophene, isobenzothiophene, benzoxazole, benzothiazole, pyrrolopyridazine, pyrrolopyrazine, and the like. Although the antenna could be any aromatic or heteroaromatic moiety, it is preferable to select one in which at least one of electronic absorption band of the antenna substantially match with at least one of the excitation or absorption band of the metal ion in order to maximize the efficiency of energy transfer from the ligand to the metal. Suitable Z groups include, but are not limited to, amino, hydroxyl, carboxyl (—COOH), carboxylate (salts of —COOH), acid halide, alkyl halides or sulfonates, sulfonyl halide, phosphoryl chloride, N-succinimido ester, chloroformate, isocyanate, acyl azide, isothiocyanate, and the like, wherein the preferred halide is chloride. Positioning of a spacer, Z', in the antenna is not critical. It would be readily apparent to the one skilled in the art that any suitable position that will accommodate a spacer/linker should be adequate as long as the distance between the antenna and metal ion and the absorption/emission wavelength is effective for energy transfer. The distance between the antenna and the metal ion is between about 2 Å and about 20 Å in some embodiments and between about 3 Å and about 10 Å in other embodiments.

Examples of Ar-Z compounds include, but are not limited to, 7-amino-4-methylcoumarin, 4-aminosalicylic acid, 1-aminonaphthalene, amninopyrazines, diaminopyrazines, pyrazine carboxylic acid, pyrazine carboxamide, 2,5-diamino-3,6-dicyanopyrazine, 3,6-diamino-2,5-pyrazinedicarboyxlic acid, 3,6-diamino-2,5-pyrazinedicarboyxlic esters, and 3,6-diamino-2,5-pyrazinedicarboxamides.

The compositions and ligands of the invention preferably contain at least one antenna. For instance, some embodiments include 1 to 3 antennae, while other embodiments include 1 to 2 antennae. Yet other embodiments may include other appropriate quantities and ranges of antennae.

In one group of compounds represented by Formula I, M is selected from Eu, Tb, Dy, Sm, Rh, Re, Ru, Cr, and In; n varies from 1 to 5; $X^1$ is an antenna; each of $X^2$ and $X^3$ is independently —O$^-$, —NH(CH$_2$)$_a$OH, —NH(CH$_2$)$_a$CO$_2$H, —NH(CH$_2$)$_a$SO$_3^-$, or —O(CH$_2$)$_a$SO$_3^-$; a ranges from 1 to 6; each of $Y^1$ and $Y^2$ is independently a single bond, —(CH$_2$)$_m$—, —(CH$_2$)$_m$O—, —(CH$_2$)$_m$OCO—, —(CH$_2$)$_m$CO$_2$—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$NHCSNH—, —(CH$_2$)$_m$OSO$_2$—, —(CH$_2$)$_m$OSO$_3^-$, —(CH$_2$)$_m$SO$_2$—, —(CH$_2$)$_m$NHSO$_2$—, or —(CH$_2$)$_m$SO$_2$NH—; m varies from 1 to 10; each of $R^1$ to $R^5$ is independently hydrogen, C1-C10 hydroxyalkyl, carboxyl, C1-C10 carboxyalkyl, —(CH$_2$)$_b$SO$_3$', —(CH$_2$)$_b$NHSO$_3^-$, —(CH$_2$)$_b$OCO(CH$_2$)$_b$SO$_3^-$, —(CH$_2$)$_b$CONH(CH$_2$)$_c$SO$_3^-$, or —(CH$_2$)$_b$NHCO(CH$_2$)$_c$SO$_3^-$; and b and c independently range from 1 to 6.

As another group of compounds represented by Formula I, M is Eu, Tb, Dy, Sm, Rh, Re, Ru, Cr or In; n varies from 1 to 5; $X^1$ is an antenna; each of $X^2$ and $X^3$ is —O$^-$; at least one of $Y^1$ and $Y^2$ is —(CH$_2$)$_m$O—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$OSO$_2$—, or —(CH$_2$)$_m$NHSO$_2$-; the other (if any) of $Y^1$ and $Y^2$ is a single bond —(CH$_2$)$_m$—, —(CH$_2$)$_m$O—, —(CH$_2$)$_m$OCO—, —(CH$_2$)$_m$CO$_2$—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$NHCSNH—, —(CH$_2$)$_m$OSO$_2$—, —(CH$_2$)$_m$OSO$_3^-$, —(CH$_2$)$_m$SO$_2$—, —(CH$_2$)$_m$NHSO$_2$—, or —(CH$_2$)$_m$SO$_2$NH—; m varies from 1 to 10; and each of $R^1$ to $R^5$ is hydrogen.

In yet another group of compounds represented by Formula I, M is Eu, Tb, Dy, Sm, Rh, Re, Ru, Cr or In; n varies from 1 to 5; each of $Y^1$ and $Y^2$ is independently a single bond, —(CH$_2$)$_m$—, —(CH$_2$)$_m$O—, —(CH$_2$)$_m$OCO—, —(CH$_2$)$_m$CO$_2$—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$NHCSNH—, —(CH$_2$)$_m$OSO$_2$—, —(CH$_2$)$_m$OSO$_3^-$, —(CH$_2$)$_m$SO$_2$—, —(CH$_2$)$_m$NHSO$_2$—, or —(CH$_2$)$_m$SO$_2$NH—; m varies from 1 to 10; $R^1$ is an antenna; each of $X^1$ to $X^3$ is independently —O$^-$, —NH(CH$_2$)$_a$OH, —NH(CH$_2$)$_a$CO$_2$H, —NH(CH$_2$)$_a$SO$_3^-$, or —O(CH$_2$)$_a$SO$_3^-$; a ranges from 1 to 6; each of $R^2$ to $R^5$ is independently hydrogen, C1-C10 hydroxyalkyl, carboxyl, C1-C10 carboxyalkyl, —(CH$_2$)$_b$SO$_3^-$, —(CH$_2$)$_b$NHSO$_3^-$, —(CH$_2$)$_b$OCO(CH$_2$)$_b$SO$_3^-$, —(CH$_2$)$_b$CONH(CH$_2$)$_c$SO$_3^-$, or —(CH$_2$)$_b$NHCO(CH$_2$)$_c$SO$_3$'; and b and c independently range from 1 to 6.

In still another group of compounds represented by Formula I, M is Eu, Tb, Dy, Sm, Rh, Re, Ru, Cr or In; n varies from 1 to 5; $R^1$ is an antenna; each of $X^1$ to $X^3$ is —O$^-$; at least one of $Y^1$ and $Y^2$ is —(CH$_2$)$_m$O—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$OSO$_2$—, or —(CH$_2$)$_m$NHSO$_2$—; the other (if any) of $Y^1$ and $Y^2$ is a single bond —(CH$_2$)$_n$-, —(CH$_2$)$_m$O—, —(CH$_2$)$_m$OCO—, —(CH$_2$)$_m$CO$_2$—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$NHCSNH—, —(CH$_2$)$_m$OSO$_2$—, —(CH$_2$)$_m$OSO$_3^-$, —(CH$_2$)$_m$SO$_2$—, —(CH$_2$)$_m$NHSO$_2$—, or —(CH$_2$)$_m$SO$_2$NH—; m varies from 1 to 10; and each of $R^2$ to $R^5$ is hydrogen.

In yet another group of compounds represented by Formula I, M is Eu, Tb, Dy, Sm, Rh, Re, Ru, Cr or In; n varies from 1 to 5; each of $Y^1$ and $Y^2$ is independently a single bond, —(CH$_2$)$_m$—, —(CH$_2$)$_m$O—, —(CH$_2$)$_m$OCO—, —(CH$_2$)$_m$CO$_2$—, —(CH$_2$).OCNH—, —(CH$_2$)$_m$OCO$_2$—, —(CH$_2$)$_m$NHCO—, —(CH$_2$)$_m$NHCONH—, —(CH$_2$)$_m$NHCSNH—, —(CH$_2$)$_m$OSO$_2$—, —(CH$_2$)$_m$OSO$_3^-$, —(CH$_2$)$_m$SO$_2$—, —(CH$_2$)$_m$NHSO$_2$—, or —(CH$_2$)$_m$SO$_2$NH—; m varies from 1 to 10; $R^2$ is an antenna; each of $X^1$ to $X^3$ is independently —O$^-$, —NH(CH$_2$)$_a$OH, —H(CH$_2$)$_a$CO$_2$H, —NH(CH$_2$)$_a$SO$_3^-$, or —O(CH$_2$)$_a$SO$_3^-$; a ranges from 1 to 6; each of $R^1$, $R^3$, $R^4$, and $R^5$ is independently hydrogen, C1-C10 hydroxyalkyl, carboxyl, C1-C10 carboxyalkyl, —(CH$_2$)$_b$SO$_3^-$, —(CH$_2$)$_b$NHSO$_3^-$, —(CH$_2$)$_b$OCO(CH$_2$)$_b$SO$_3^-$, —(CH$_2$)$_b$CONH(CH$_2$)$_c$SO$_3^-$, or —(CH$_2$)$_b$NHCO(CH$_2$)$_c$SO$_3^-$; and b and c independently range from 1 to 6.

In yet another group of compounds represented by Formula I, M is Eu, Tb, Dy, Sm, Rh, Re, Ru, Cr, or In; n varies from 1 to 5; $R^2$ is an antenna; each of $X^1$ to $X^3$ is —O$^-$; at least one of $Y^1$ and $Y^2$ is —(CH$_2$)$_m$O—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$OSO$_2$—, and —(CH$_2$)$_m$NHSO$_2$—; the other (if any) of $Y^1$ and $Y^2$ is a single bond —(CH$_2$)$_m$—, —(CH$_2$)$_m$O—, —(CH$_2$)$_m$OCO—, —(CH$_2$)$_m$CO$_2$—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$NHCSNH—, —(CH$_2$)$_m$OSO$_2$—, —(CH$_2$)$_m$OSO$_3^-$, —(CH$_2$)$_m$SO$_2$—, —(CH$_2$)$_m$NHSO$_2$—, or —(CH$_2$)$_m$SO$_2$NH—; m varies from 1 to 10; and each of $R^1$, $R^3$, $R^4$, and $R^5$ is hydrogen.

In still yet another group of compounds represented by Formula I, M is Eu, Tb, Dy, Sm, Rh, Re, Ru, Cr, or In; n varies from 1 to 5; $R^3$ is an antenna; each of $X^1$ to $X^3$ is independently —O$^-$, —NH(CH$_2$)$_a$OH, —NH(CH$_2$)$_a$CO$_2$H, —NH(CH$_2$)$_a$SO$_3^-$, or —O(CH$_2$)$_a$SO$_3^-$; a ranges from 1 to 6; at least one of $Y^1$ and $Y^2$ is independently a single bond or a spacer group; m varies from 1 to 10; each of $R^1$, $R^2$, $R^4$, and $R^5$ is independently hydrogen, C1-C10 hydroxyalkyl, carboxyl, C1-C10 carboxyalkyl, —(CH$_2$)$_b$SO$_3^-$, —(CH$_2$)$_b$NHSO$_3^-$, —(CH$_2$)$_b$OCO(CH$_2$)$_b$SO$_3^-$, —(CH$_2$)$_b$CONH(CH$_2$),SO$_3^-$, or —(CH$_2$)$_b$NHCO(CH$_2$)$_c$SO$_3^-$; and b and c independently range from 1 to 6.

In still a further group of compounds represented by Formula I, M is Eu, Tb, Dy, Sm, Rh, Re, Ru, Cr, or In; n varies from 1 to 5; $R^3$ is an antenna; each of $X^1$ to $X^3$ is —O$^-$; at least one of Y, and $Y^2$ is independently —(CH$_2$)$_m$O—, —(CH$_2$)$_m$OCNH—, —(CH$_2$)$_m$OCO$_2$—, —(CH$_2$)$_m$NHCO—, —(CH$_2$)$_m$NHCONH—, —(CH$_2$)$_m$OSO$_2$—, or —(CH$_2$)$_m$NHSO$_2$—; the other (if any) of $Y^1$ and $Y^2$ is a spacer; m varies from 1 to 10; and each of $R^1$, $R^2$, $R^4$, and $R^5$ is hydrogen.

The antennae of the present invention can be attached to the DTPA at the five carboxyl groups or at the nine methylene positions in Formula I by conventional methods well known in the art [28, 29]. For example, the attachment at the carboxyl position can be accomplished by first reacting DTPA dianhydride (8) with the antenna bearing a hydroxyl or an amino group to give the corresponding ester and amide ligands followed by metal complexation to give the complexes 9 or 10 respectively (FIG. 3)[30-32]. The metal complexation of polyaminocarboxylate ligands are typically accomplished using the desired metal oxide, metal carbonate, metal halide or other metal salts, and weak complexes such as acetylacetonate, and the like.

Figure 4:
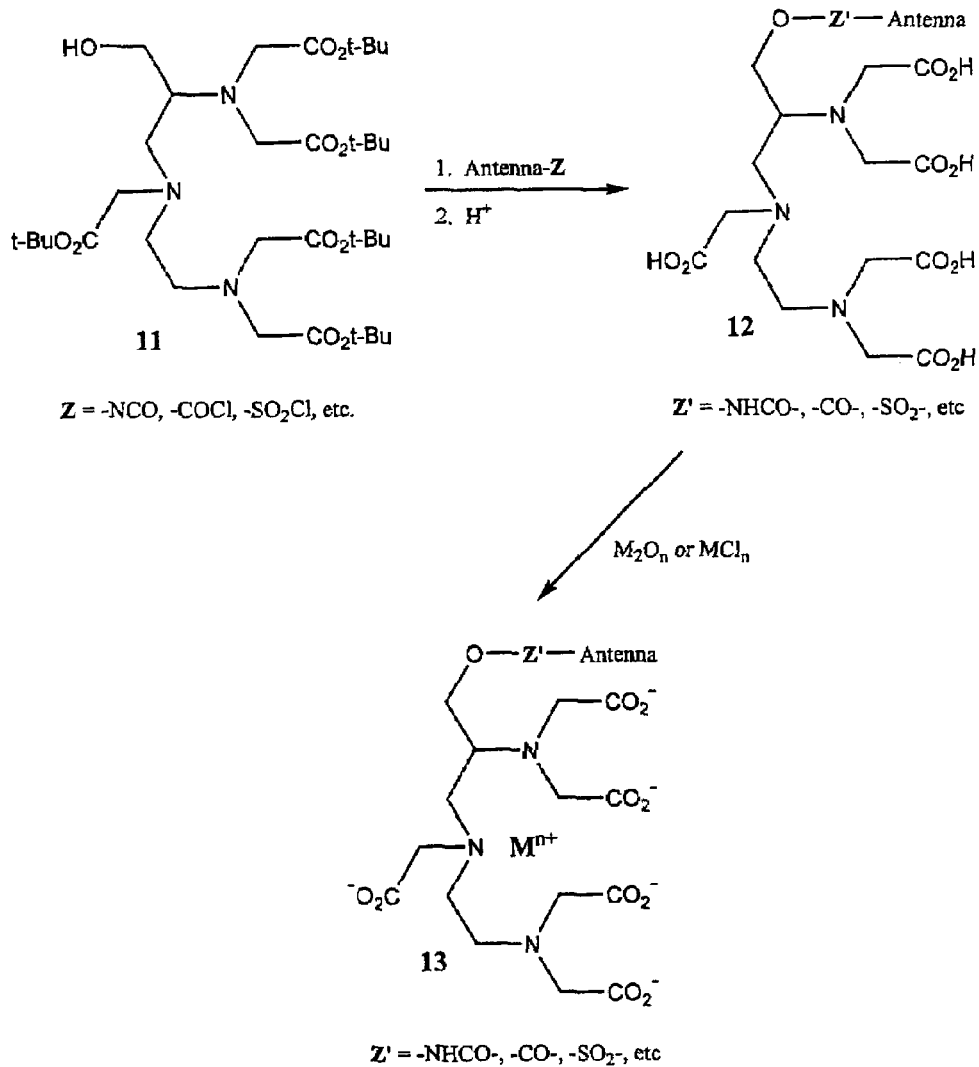
FIG. 4: Attachment of the antenna at the β-position in the ethylene unit of DTPA.

The attachment of an antenna to the carbon atom to the ethylene unit on the carbon at the D position to the central nitrogen of DTPA can be accomplished by condensing the known hydroxymethyl-DTPA derivative 11 [33] with Ar-Z, i.e. the antennae containing reactive linking groups (also referred to as 'handles') such as carboxyl, acid halide, alkyl halides or sulfonates, sulfonyl halide, phosphoryl chloride, N-succinimido ester, chloroformate, isocyanate, acyl azide, isothiocyanate, and the like (FIG. 4). The metal complexation of the resulting ligand 12 can be carried out in the same manner as described above to give complex 13.

Figure 5:
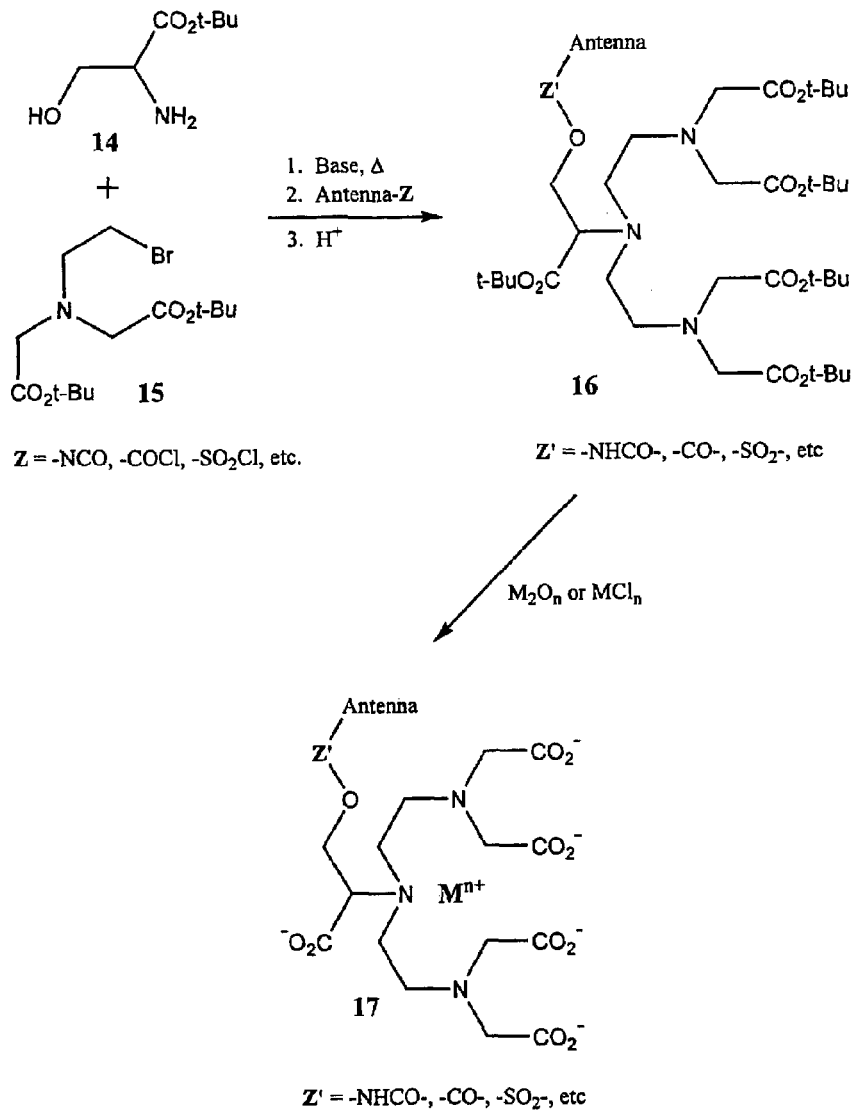
FIG. 5: Attachment of the antenna at the α-carbon to the central acetate of DTPA.

The attachment of an antenna to the carbon atom at the a position to the carboxyl group of the acetate residue attached to the central nitrogen can be accomplished by introducing the hydroxymethyl group at this position as described in FIG. 5. Alkylation of serine t-butylester (14) [34] with N-(2-bromo)ethyliminodiacetate (15)[35], followed by condensation of the hydroxyl group with the antennae containing reactive linking groups mentioned previously provides the ligand 16. The metal complexation of ligand 16 can be carried out in the same manner as described above to give 17.

Figure 6:
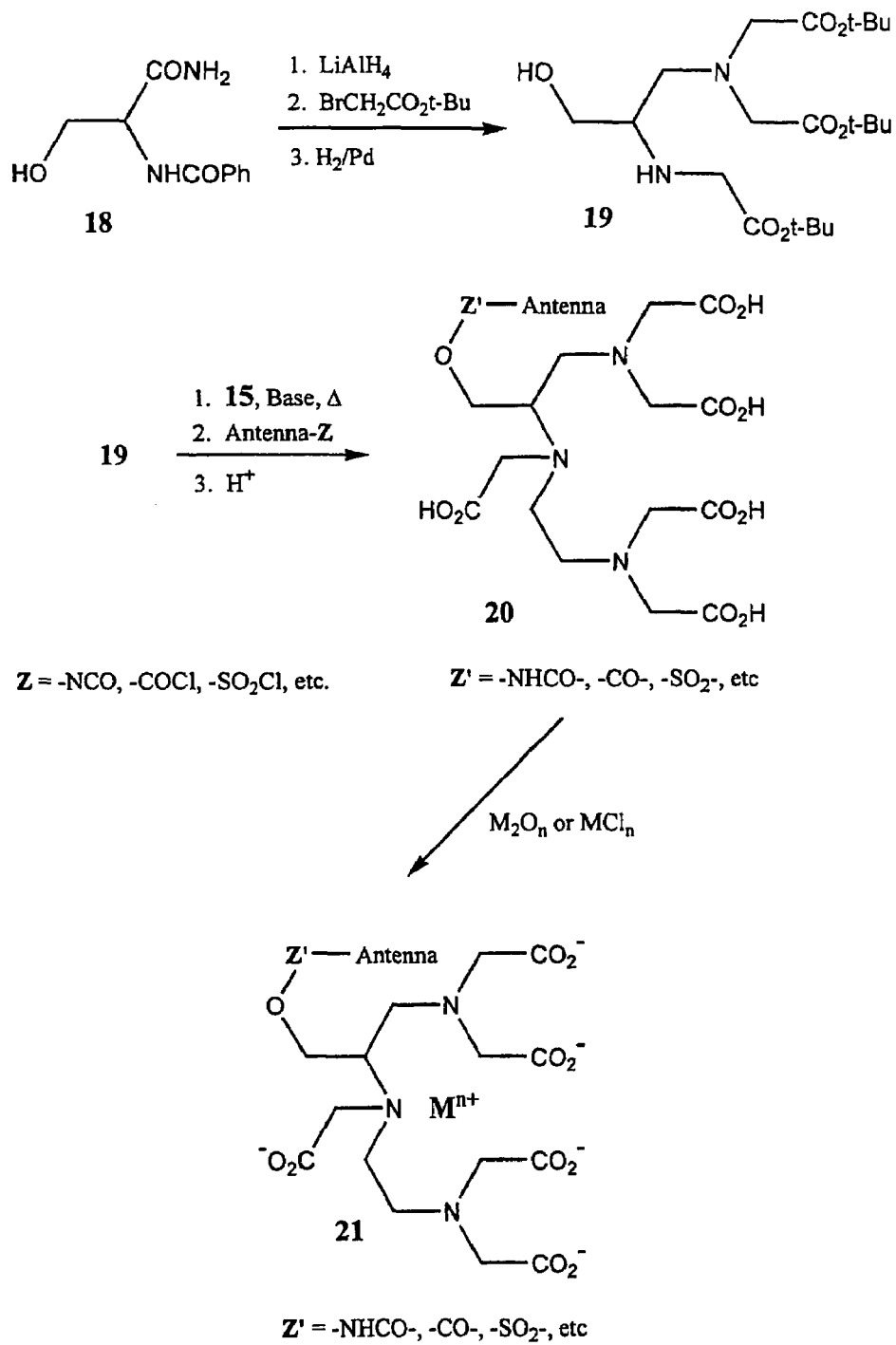
FIG. 6: Attachment of the antenna at the α-position in the ethylene unit of DTPA.

The attachment of antenna to the carbon atom of the ethylene unit at the a position to the central nitrogen can be effected by first preparing the hydroxymethyl intermediate 19 from N-benzoylserinamide (18) and alkylating it with N-(2-bromo)ethyliminodiacetate 15 followed by condensation of the resulting hydroxymethyl derivative with the antennae (FIG. 6). The metal complexation of ligand 20 can be carried out in the same manner as described above to give 21. One of the advantages of at least some embodiments of the present invention is that the synthetic method may be carried out in a modular fashion so as to allow for preparation of a wide variety of DTPA-antenna conjugates in a simple and rapid manner. Hydroxymethyl-DTPA derivatives tend to be versatile intermediates in that the hydroxyl group can be transformed into various other functionalities such as amino, formyl, or carboxyl, which can further serve as a handle to link the antennae endowed with complementary functional groups.

In accordance with the present invention, one protocol for measuring physiological functions of body cells includes selecting a suitable DTPA complex from the compositions of Formula I (hereinafter referred to as 'tracers') capable of absorbing and emitting electromagnetic radiation at different wavelengths, administering an effective amount of the tracer into a patient's body, detecting signal emanating from the tracer by invasive or non-invasive optical probes, determining the signal intensity over time as necessitated by the clinical condition, and correlating an intensity-time profile with a physiological or pathological condition of the patient.

The antennae of the present invention may vary widely depending on the metal ion of interest and on the detection apparatus employed. The DTPA derivatives of the present invention may optionally contain more than one light absorbing or emitting units for increasing the sensitivity of detection. The dosage is readily determined by one of ordinary skill in the art and may vary according to the clinical procedure contemplated, generally ranging from 1 nanomolar to 100 micromolar. The tracers may be administered to the patient by any suitable method, including intravenous, intraperitoneal, or subcutaneous injection or infusion, oral administration, transdermal absorption through the skin, or by inhalation. The detection of the tracers is achieved by optical fluorescence, absorbance, or light scattering methods known in the art using invasive or non-invasive probes such as endoscopes, catheters, ear clips, hand bands, head bands, surface coils, finger probes, and the like [37]. Physiological function may be correlated with clearance profiles and rates of these agents from the body fluids [38].

Organ function can be assessed by comparing differences in the manner in which normal and impaired cells remove the tracer from the bloodstream, by measuring the clearance or accumulation of these tracers in the organs or tissues, and/or by obtaining tomographic images of the organs or tissues. Blood pool clearance may be measured non-invasively from convenient surface capillaries such as those found in an ear lobe or a finger or can be measured invasively using an endovascular catheter. Accumulation of the tracer within the cells of interest can be assessed in a similar fashion. The clearance of the tracer compounds can be determined by selecting excitation wavelengths and filters for the emitted photons. The concentration/time curves may be analyzed (preferably, but not necessarily in real time) by a microprocessor or the like.

In addition to noninvasive techniques, a modified pulmonary artery catheter that can be used to make desired measurements has been developed [39]. This is a distinct improvement over current pulmonary artery catheters that measure only intravascular pressures, cardiac output and other derived measures of blood flow. Current critically ill patients are managed using these parameters but rely on intermittent blood sampling and testing for assessment of renal function. These laboratory parameters represent discontinuous data and are frequently misleading in many patient populations. Yet, importantly, they are relied upon heavily for patient assessment, treatment decisions, and drug dosing.

The modified pulmonary artery catheter incorporates an optical sensor into the tip of a standard pulmonary artery catheter. This wavelength-specific optical sensor can monitor the renal function specific elimination of a designed optically detectable chemical entity. Thus, by a method substantially analogous to a dye dilution curve, real-time renal function can be monitored by the disappearance of the optically detected compound. Appropriate modification of a standard pulmonary artery catheter generally includes merely making the fiber optic sensor wavelength-specific. Catheters that incorporate fiber optic technology for measuring mixed venous oxygen saturation exist currently.

The following examples illustrate specific embodiments of the invention. As would be apparent to skilled artisans, various changes and modifications are possible and are contemplated within the scope of the invention described.

EXAMPLE 1

Preparation and biodistribution of $^{99m}$Tc-DTPA.

Figure 7:
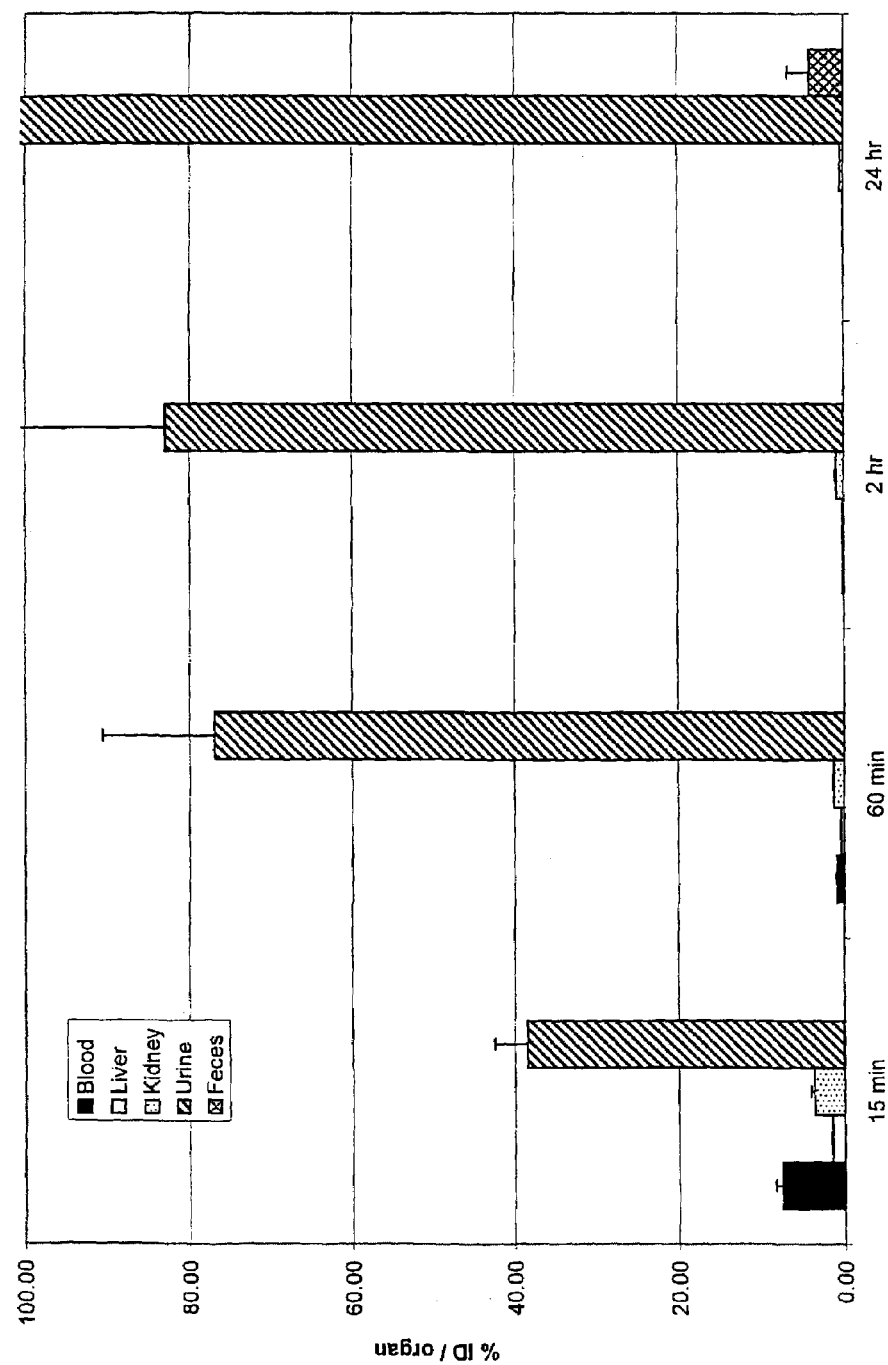
FIG. 7: Bar graph of normal rat biodistribution of Tc-DTPA.

Commercially available DTPA kit (Draximage Co., Ontario, Canada) was labeled with $^{99m}$Tc by the standard procedure described in the package insert that was supplied with the kit, and was administered to Sprague-Dawley rats (3 rats for each time point of 15 minutes, 60 minutes, 120 minutes, and 24 hours). The biodistribution data, shown in FIG. 7, serves as a positive control for determining whether the novel compounds of the present invention clear via glomerular filtration.

EXAMPLE 2

Preparation and biodistribution of compound of Formula I wherein $X^2$ is —O$^-$; $X^3$ and $R^1$ to $R^5$ are hydrogens; $M^{n+}$ is $^{111}$In$^{3+}$ and $X^1$ is an antenna derived from 7-amino-4-methylcoumarin; and $Y^1$ and $Y^2$ are single bonds.

Figure 8:
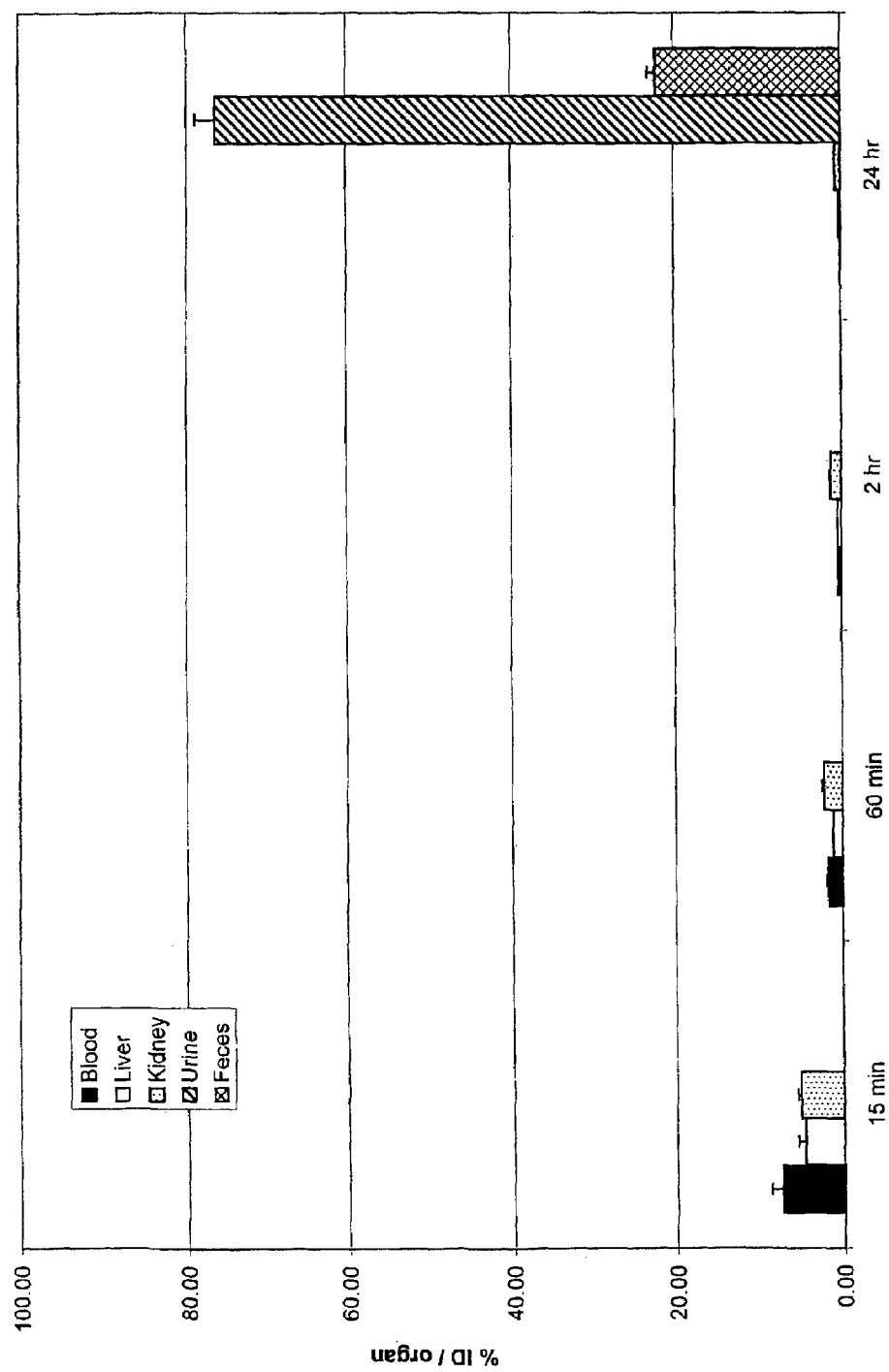
FIG. 8: Bar graph of normal rat biodistribution of $^{111}$In-DTPA-mono(coumarin amide) complex.

A mixture of the stock solution of DTPA-mono(7-amino-4-methylcoumarin)amide ligand (1 mg/mL in 0.5M sodium acetate buffer, 100 µL), obtained from Gunma University, Japan (Ozaki, et. al. Reference 30), sodium acetate solution (0.5M, 100 µL), and commercially available $^{111}$InCl$_3$ solution (0.1M HCl, 100-200 µCi/100 µL) was adjusted to pH 4.5 and incubated at ambient temperature for 30 minutes. The resulting indium complex was purified by reverse phase HPLC and administered to Sprague-Dawley rats. The biodistribution was carried out in the same manner as that of $^{99m}$Tc-DTPA in Example 1 (FIG. 8). This indium complex exhibited slightly more hepatobiliary clearance than $^{99m}$Tc-DTPA, but cleared substantially through the kidneys.

EXAMPLE 3

Preparation and biodistribution of compound of Formula I, wherein $X^2$, $X^3$ and $R^1$ to $R^5$ are hydrogens; $M^{n+}$ is $^{111}In^{3+}$, and $X^1$ is an antenna derived from 4-aminosalicylic acid-, and $Y^1$ and $Y^2$ are single bonds.

Figure 9:
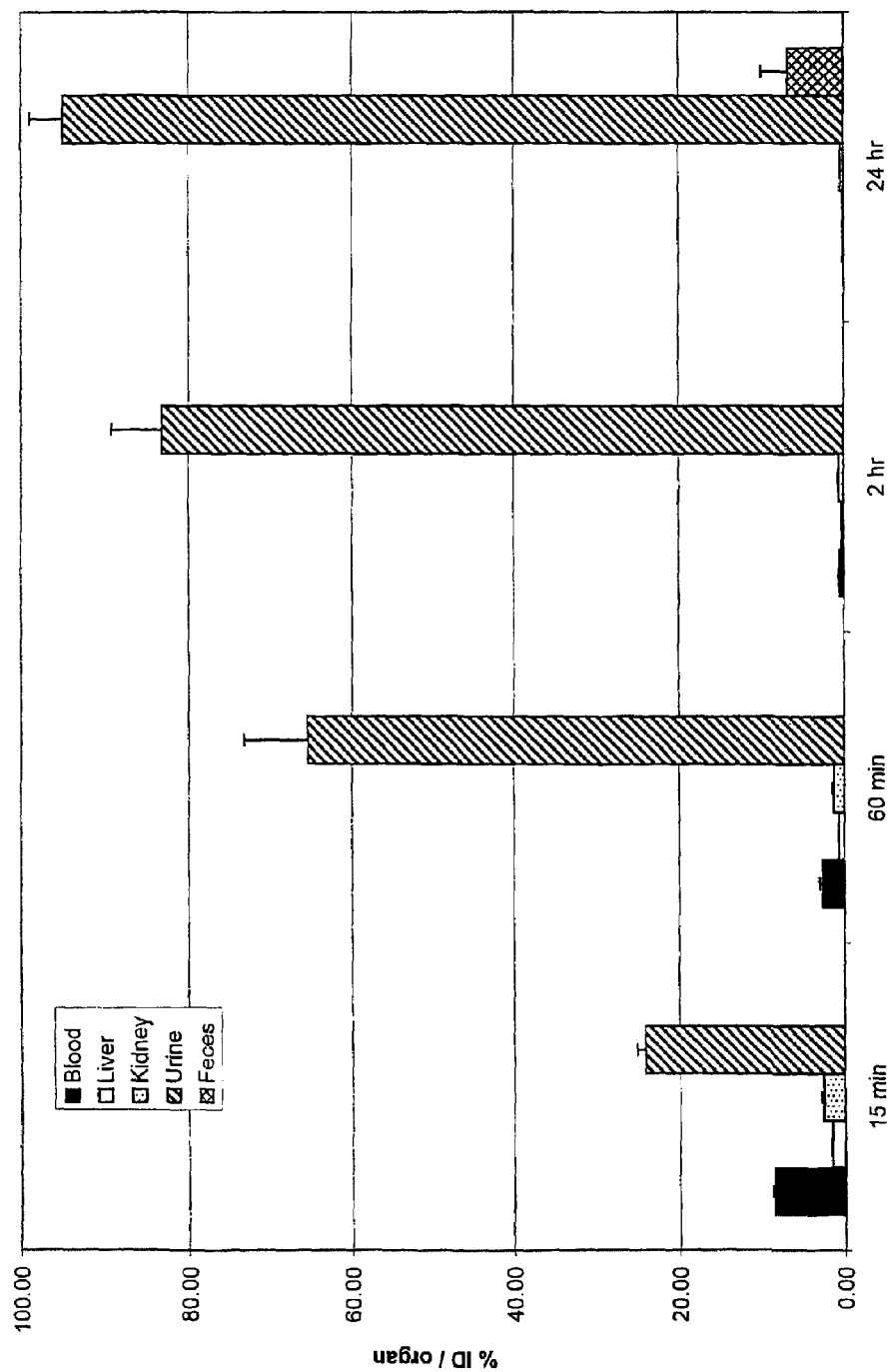
FIG. 9: Bar graph of normal rat biodistribution of $^{111}$In-DTPA-mono(salicylamide) complex.

The DTPA-mono(4-aminosalicyl)amide ligand was obtained from Gunma University, Japan (Ozaki, et. al. Reference 30). The indium labeling and biodistribution of this ligand is carried out in the same manner as in Example 2. The biodistribution of this complex (FIG. 9) is nearly identical to that of $^{99m}Tc$-DTPA.

EXAMPLE 4

Preparation and biodistribution of compound of Formula I, wherein $X^2$ is —O$^-$, $X^3$ and $R^1$ to $R^5$ are hydroyens; $M^{n+}$ is $^{111}In^{3+}$; $X^1$ is an antenna derived from 1-aminonaphthalene; and $Y^1$ and $Y^2$ are single bonds.

Figure 10:
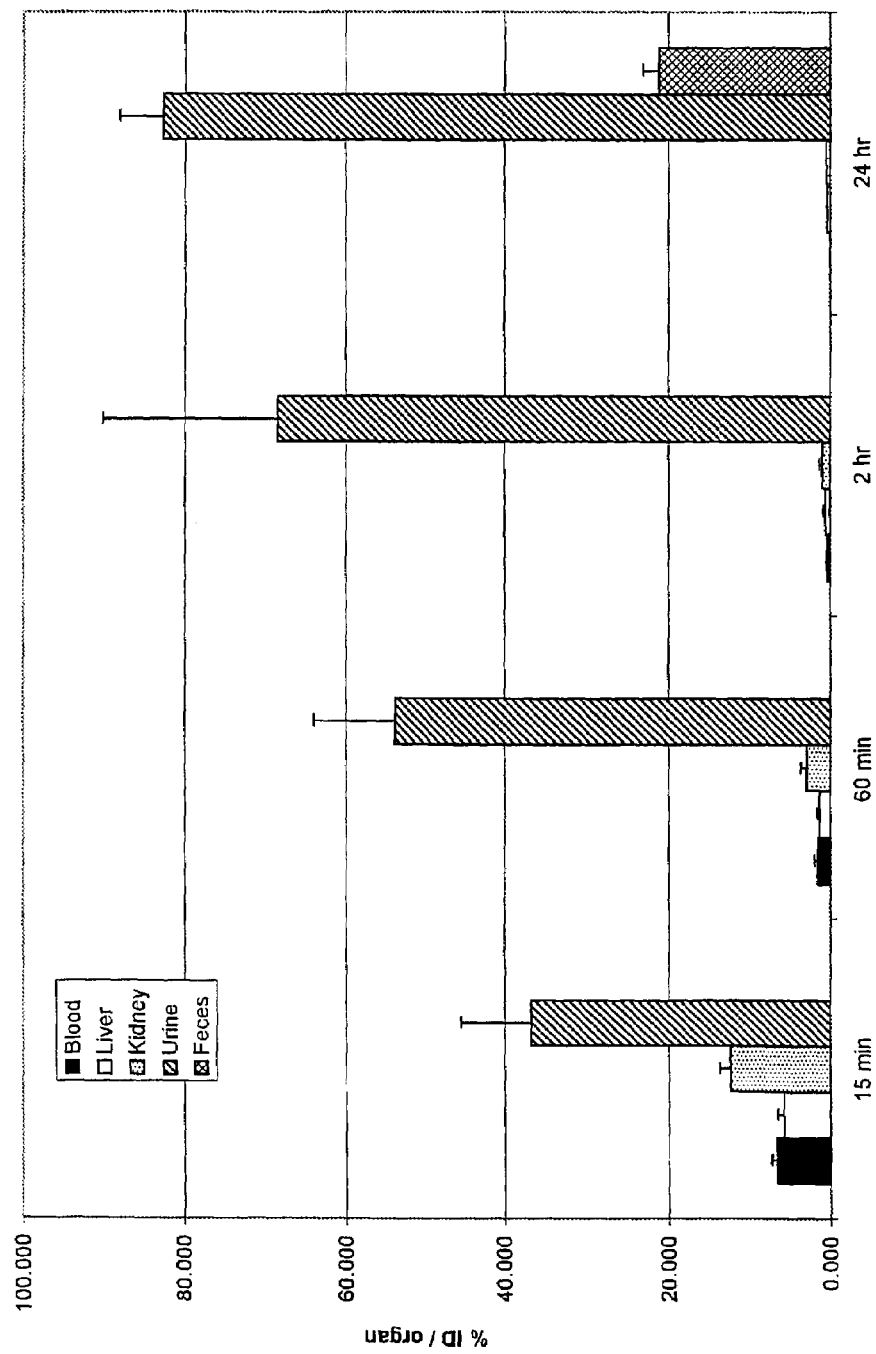
FIG. 10: Bar graph of normal rat biodistribution of $^{111}$In-DTPA-mono(1-naphthylamide) complex.

The DTPA-mono(l-aminonaphthyl)amide ligand was obtained from Gunma University, Japan (Ozaki, et. al. Reference 30). The indium labeling and biodistribution of this ligand is carried out in the same manner as in Example 2. The biodistribution of this complex (FIG. 10) is nearly identical to that of $^{99m}Tc$-DTPA.

EXAMPLE 5

Preparation and biodistribution of compound of Formula I, wherein $X^1$ to $X^3$ and $R^2$ to $R^5$ are hydrogens; $M^{n+}$ is $In^{3+}$; $R^1$ is an antenna derived from 1-aminonaphthalene: $Y^1$ is —CH$_2$O—; and $Y^2$ is a single bond.

Step 1. A mixture of the hydroxymethyl-DTPA (11) 100 mg (0.1 mmol) and 1-naphthylisocyanate (101 mg, 1.0 mmol) in toluene (20 mL) was heated under reflux for 16 hours. The solvent was evaporated in vacuo and the residue was purified by flash chromatography (Argonaut Flashmaster Solo) using hexanes/ethylacetate as eluent (linear gradient: 0% to 75% ethylacetate in 40 minutes) to give the DTPA-1-naphthylurethane derivative as the penta-t-butylester.

Step 2. The pentaester from Step 1 (1.2 g) was dissolved in 96% formic acid (10 mL) and heated until boiling and thereafter kept at ambient temperature for 16 hours. The solution was poured onto ether (500 mL). The gummy residue was separated from the bulk solvent by decantation and was purified by reverse phase flash chromatograpy (Argonaut Flashmaster Solo) to give the desired ligand.

Figure 11:
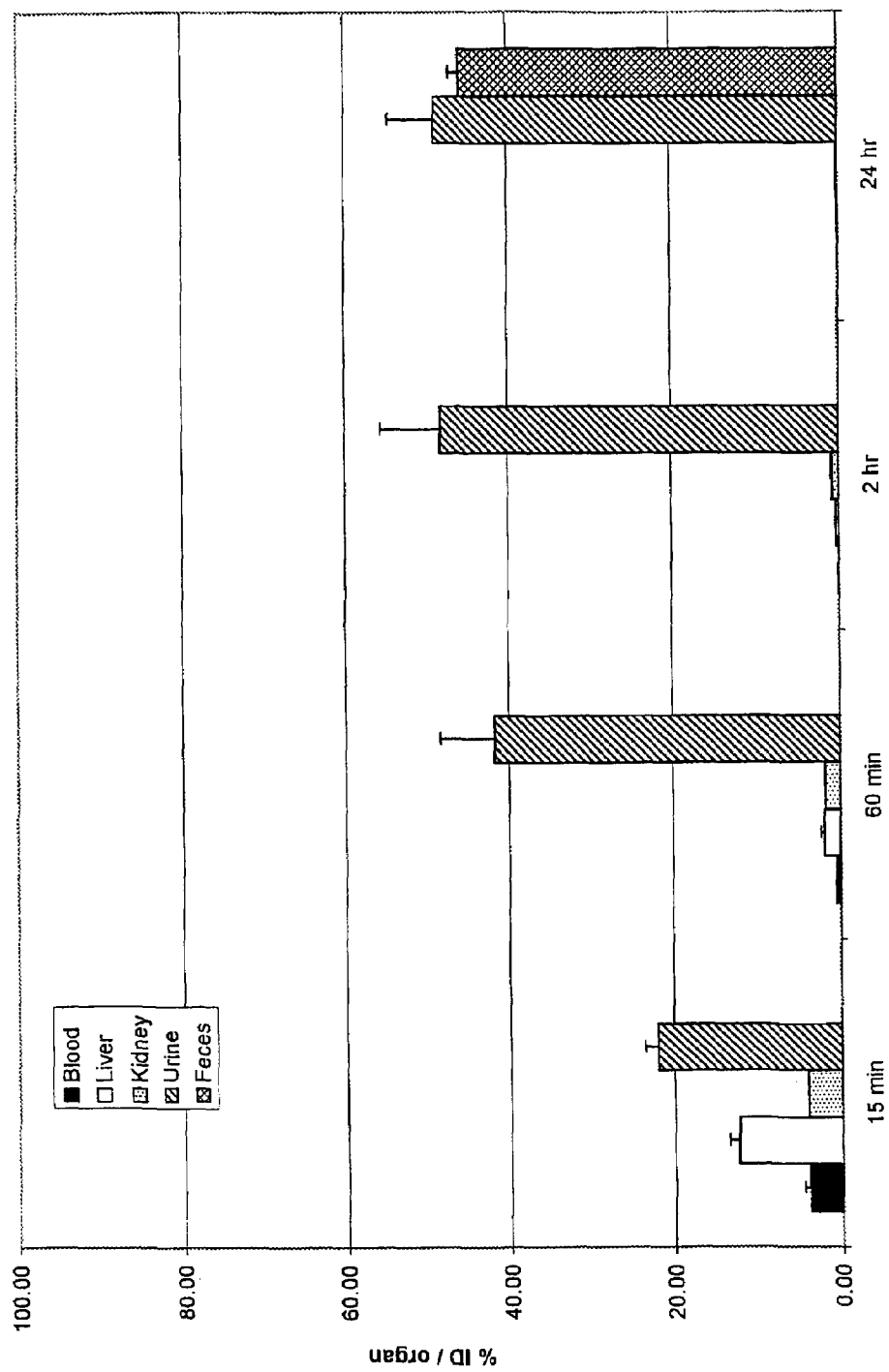
FIG. 11: Bar graph of normal rat biodistribution of $^{111}$In-HMDTPA-1-naphthylurethane complex.

Step 3. The indium labeling and biodistribution of this ligand is carried out in the same manner as in Example 2. The biodistribution of this complex (FIG. 11) is similar to that of $^{111}In$-DTPA-coumarin derivative in Example 2, with much higher hepatobiliary clearance.

EXAMPLE 6

Preparation and biodistribution of compound of Formula I, wherein $X^3$ and $R^1$ to $R^5$ are hydrogens; $M^{n+}$ is $^{111}In^{3+}$; $X^1$ and $X^2$ are antennae derived from 4-aminosalicylic acid, and $Y^1$ and $Y^2$ are single bonds.

Figure 12:
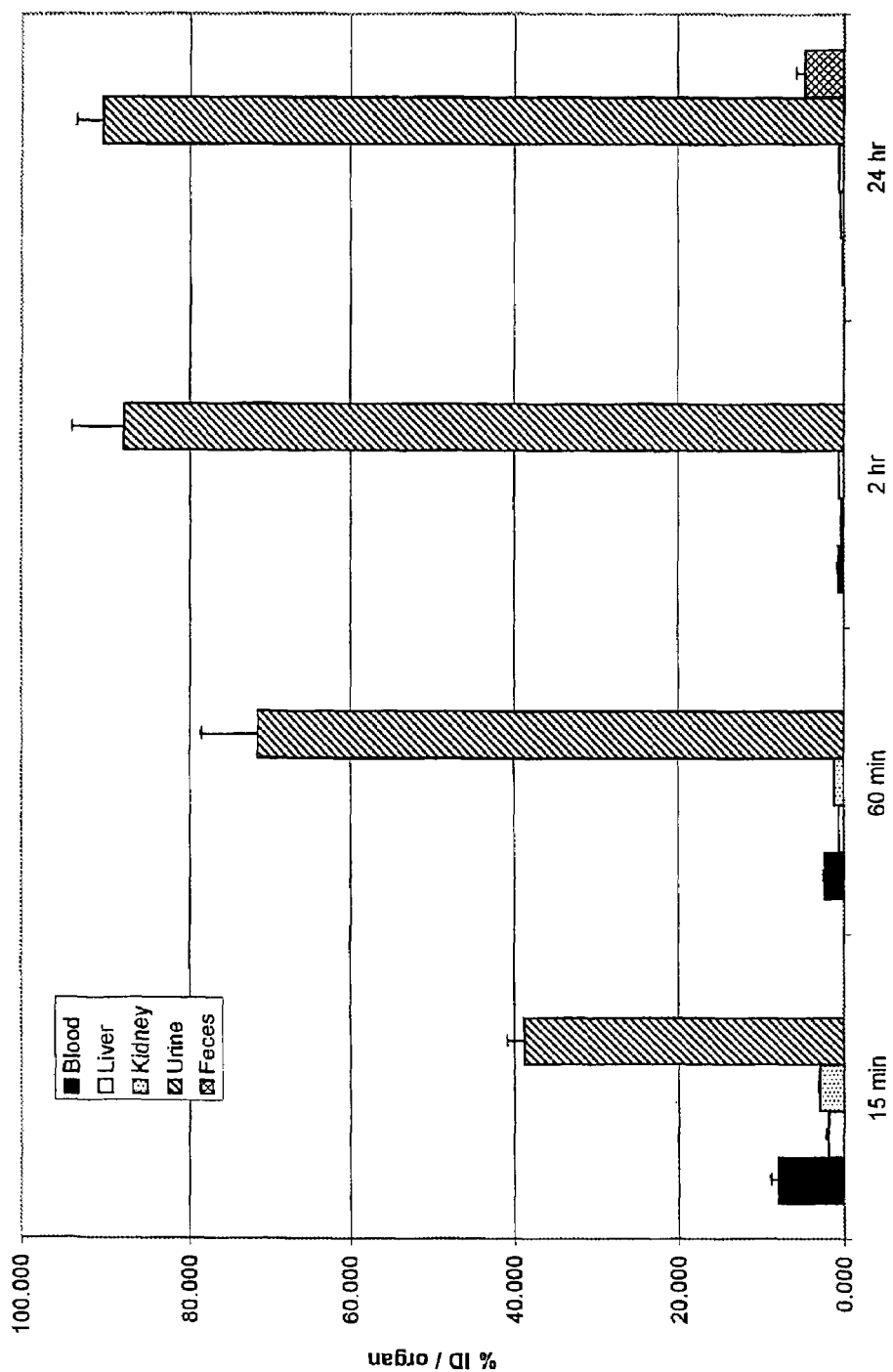
FIG. 12: Bar graph of normal rat biodistribution of $^{111}$In-DTPA-bis(salicylamide) complex.

The DTPA-bis(4-aminosalicyl)amide ligand was obtained from Gunma University, Japan (Ozaki, et. al. Reference 30). The indium labeling and biodistribution of this ligand is carried out in the same manner as in Example 2. The biodistribution of this complex (FIG. 12) is nearly identical to that of $^{99m}Tc$-DTPA.

EXAMPLE 7

Preparation and biodistribution of compound of Formula I, wherein $X^3$ and $R^1$ to $R^5$ are hydrogens, $M^{n+}$ is $^{111}In^{3+}$, $X^1$ and $X^2$ are antennae derived from 2-(N-2-aminoethyl)-aminopyrazine and $Y^1$ and $Y^2$ are single bonds.

A mixture of DTPA-bisanhydride 0.45 g. (1.3 mmol) and N,N'-dimethyl-N-pyrazin-2-ylethane-1,2-diamine 0.42 g. (2.5 mmol) in anhydrous DMSO (8 mL) was heated at 50-55° C. for 1 hour and stirred at room temperature for another 16 hours. The crude product was precipitated in acetone (100 mL) and the residue purified by reversed phase flash chromatography (Argonaut Flashmaster Solo) using deionized water as eluant followed by evaporation of water to give the desired bisamide ligand.

The indium labeling and biodistribution of this ligand was carried out in the same manner as in Example 2. The biodistribution of this complex (FIG. 13) is nearly identical to that of $^{99m}Tc$-DTPA.

EXAMPLE 8

Preparation and biodistribution of compound of Formula I, wherein $X^2$ is —O$^-$; $X^3$ and $R^1$ to $R^5$ are hydrogens: $M^{n+}$ is $^{111}In^{3+}$; $X^1$ is an antenna derived from 2-carboxy-3-(2-aminoethyl)aminoquinoxaline;

and $Y^1$ and $Y^2$ are single bonds.

A mixture of DTPA-bisanhydride 0.20 g. (0.6 mmol) and 3-[(2-aminoethyl)amino]-quinoxaline-2-carboxylic acid hydrochloride 0.30 g. (1.1 mmol) in triethylamine (1.5 mL) and anhydrous DMSO (5 mL) was heated at 50-55° C. for 4 hours and stirred at room temperature for another 16 hours. The crude product was precipitated in acetone (100 mL) and the residue solution was acidified to pH 3 with dilute hydrochloric acid, then purified by reversed phase flash chromatography (Argonaut Flashmaster Solo) using deionized water/acetonitrile eluent gradient (0% to 20% acetonitrile over 30 minutes), followed by evaporation of solvents to give the desired monoamide ligand.

The indium labeling and biodistribution of this ligand was carried out in the same manner as in Example 2. The biodistribution of this complex (FIG. 14) is nearly identical to that of the DTPA-coumarin derivative in Example 2.

These examples demonstrate that GFR agents based on polyaminocarboxylate metal complexes with the appropriate selection of antenna group(s) would be effective as renal function agents and would provide clearance properties similar to those of Tc-DTPA. In particular, previous data on Eu-DTPA-coumarin complex based on the ligand used in Example 2 showed that the coumarin antenna enhances europium fluorescence by about 1000-fold [30]. The data of the present invention showed that this complex has clearance properties similar to that of Tc-DTPA, but with more hepatobiliary clearance. Thus, introduction of appropriate hydrophilic functionalities in the coumarin ring would make the complex clear in the same manner as Tc-DTPA. Furthermore, hydrophilic antenna similar in size to the coumarin moiety and that matches the excitation wavelengths of europium metal can be readily attached to the DTPA portion to achieve optimal fluorescence and clearance properties.

The examples further demonstrate that at least some compounds of the invention have antennae that are cleared through the kidneys by the GFR mechanism with hepatobiliary clearance comparable to that with $^{99m}$Tc-DTPA, i.e. hepatobiliary clearance essentially no greater than that with $^{99m}$Tc-DTPA. In addition, compounds that are cleared through the kidneys by the GFR mechanism but that have hepatobiliary clearance that is greater than that with $^{99m}$Tc-DTPA have been found to be capable of clearing essentially like $^{99m}$Tc-DTPA by adding a W substituent group to the antenna.

REFERENCES

1. Nally, J. V. Acute renal failure in hospitalized patients. *Cleveland Clinic Journal of Medicine* 2002, 69(7), 569-574.
2. C. A. Rabito, L. S. T. Fang, and A. C. Waltman. Renal function in patients at risk with contrast material-induced acute renal failure: Noninvasive real-time monitoring. *Radiology* 1993, 186, 851-854.
3. N. L. Tilney, and J. M. Lazarus. Acute renal failure in surgical patients: Causes, clinical patterns, and care. *Surgical Clinics of North America* 1983, 63, 357-377.
4. B. E. VanZee, W. E. Hoy, and J. R. Jaenike. Renal injury associated with intravenous pyelography in non-diabetic and diabetic patients. *Annals of Internal Medicine* 1978, 89, 51-54.
5. S. Lundqvist, G. Edbom, S. Groth, U. Stendahl, and S.-O. Hietala. Iohexol clearance for renal function measurement in gynecologic cancer patients. *Acta Radiologica* 1996, 37, 582-586.
6. P. Guesry, L. Kaufman, S. Orloff, J. A. Nelson, S. Swann, and M. Holliday. Measurement of glomerular filtration rate by fluorescent excitation of non-radioactive meglumine iothalamate. *Clinical Nephrology* 1975, 3, 134-138).
7. C. C. Baker et al. Epidemiology of Trauma Deaths. *American Journal of Surgery* 1980, 144-150.
8. R. G. Lobenhoffer et al. Treatment Results of Patients with Multiple Trauma: An Analysis of 3406 Cases Treated Between 1972 and 1991 at a German Level I Trauma Center. *Journal of Trauma* 1995, 38, 70-77.
9. J. Coalson, Pathology of Sepsis, Septic Shock, and Multiple Organ Failure. In *New Horizons: Multiple Organ Failure*, D. J. Bihari and F. B. Cerra, (Eds). Society of Critical Care Medicine, Fullerton, Calif., 1986, pp. 27-59.
10. F. B. Cerra, Multiple Organ Failure Syndrome. In *New Horizons: Multiple Organ Failure*, D. J Bihari and F. B. Cerra, (Eds). Society of Critical Care Medicine, Fullerton, Calif., 1989, pp. 1-24.
11. R. Muller-Suur, and C. Muller-Suur. Glomerular filtration and tubular secretion of MAG$_3$ in rat kidney. *Journal of Nuclear Medicine* 1989, 30, 1986-1991).
12. P. D. Dollan, E. L. Alpen, and G. B. Theil. A clinical appraisal of the plasma concentration and endogenous clearance of creatinine. *American Journal of Medicine* 1962, 32, 65-79.
13. J. B. Henry (Ed). *Clinical Diagnosis and Management by Laboratory Methods*, 17th Edition, W. B. Saunders, Philadelphia, Pa., 1984.
14. F. Roch-Ramel, K. Besseghir, and H. Murer. Renal excretion and tubular transport of organic anions and cations. In *Handbook of Physiology, Section 8, Neurological Physiology, Vol. II*, E. E. Windhager, Editor, pp. 2189-2262. Oxford University Press: New York, 1992
15. G. Ekanoyan and N. W. Levin. In *Clinical Practice Guidelines for Chronic Kidney Disease: Evaluation, Classification, and Stratification (K/DOQI)*. National Kidney Foundation: Washington, D.C. 2002, pp. 1-22.
16. D. L. Nosco and J. A. Beaty-Nosco. Chemistry of technetium radiopharmaceuticals 1: Chemistry behind the development of technetium-99m compounds to determine kidney function. *Coordination Chemistry Reviews* 1999, 184, 91-123.
17. P. L. Choyke, H. A. Austin, and J. A. Frank. Hydrated clearance of gadolinium-DTPA as a measurement of glomerular filtration rate. *Kidney International* 1992, 41, 1595-1598.
18. N. Lewis, R. Kerr, and C. Van Buren. Comparative evaluntion of urographic contrast media, inulin, and $^{99m}$Tc-DTPA clearance methods for determination of glomerular filtration rate in clinical transplantation. *Transplantation* 1989, 48, 790-796).
19. W. N. Tauxe. Tubular Function. In *Nuclear Medicine in Clinical Urology and Nephrology*, W. N. Tauxe and E. V. Dubovsky, Editors, pp. 77-105, Appleton Century Crofts: East Norwalk, 1985.
20. A. R. Fritzberg et al. Mercaptoacetylglycylglycyglycine. *Journal of Nuclear Medicine* 1986, 27, 111-120.
21. Rajagopalan, R. et al. Quinoline ligands and metal complexes for diagnosis and therapy. U.S. Patent 2001; 6,277, 841.
22. Rabito, C. Fluorescent agents for real-time measurement of organ function. U.S. Patent 2002; 6,440,389.
23. M. F. Tweedle, X. Zhang, M. Fernandez, P. Wedeking, A. D. Nunn, A. D. and H. W. Strauss. A noninvasive method for monitoring renal status as bedside. *Investigative Radiology* 1997, 32, 802-805.
24. J. R. Lacowicz. Energy transfer. In *Principles of Fluorescence Spectroscopy, pp. 303-339*. Plenum: New York, N.Y., 1983.
25. A. Abusaleh and Meares, C. F. Excitation and deexcitation process in lanthanide chelates bearing aromatic side chains. *Photochemistry and Photobiology* 1984, 39(6), 763-769.
26. Gunnlaugsson, T., Parker, D. Luminescent europium tetraazamacrocyclic complexes with wide range pH sensitivity. *Chemical Communications* 1998, 511-512.
27. Chen, J., Selvin, P. R. Thiol-reactive luminescent chelates of terbium and europium. *Bioconjugate Chemistry* 1999, 10(2),311-315.
28. Wenzel, T. G. et al. "Bifunctional" chelating agents for binding metal ions to proteins. *Radioimmunoimaging and Radioimmunotherapy* 1983, 185-196.
29. Chang, C. H et al. Bifunctional chelating agents: linking radiometals to biological membranes. *Applied Nuclear and Radiochemistry* 1982, 103-114.
30. Ozaki, H. et al. Sensitization of europium(III) luminescence by DTPA derivatives. *Chemistry Letters* 2000, 312-313.
31. Geraldes, C. F. G. C. et al. Preparation, physicochemical characterization, and relaxometry studies of various gadolinium(III)-DTPA-bis(amide) derivatives as potential magnetic resonance contrast agents. *Magnetic Resonance Imaging* 1995, 13(3), 401-420.
32. Konings, M. S. et al. Gadolinium complexation by a new diethylenetriaminepentaacetic acid ligand. Amide oxygen coordination. *Inorganic Chemistry* 1990, 29(8), 1488-1491.
33. Amedio, J. C. et al. A practical manufacturing synthesis of 1-(R)-hydroxymethyl-DTPA: an important intermediate in the synthesis of MRI contrast agents. *Synthetic Communications* 1999, 29(14), 2377-2391.

34. Pickersgill, I. F. and Rapoport, H. Preparation of functionalized, conformationally constrained DTPA anlogues from L- or D-serine and trans-4-hydroxyproline. Hydroxymethyl substituents on the central acetic acid and on the backbone. *Journal of Organic Chemistry* 2000, 65, 4048-4057.

35. Achilefu, S., and Srinivasan, A. Methods for incorporating metal chelators at carboxyl-terminal site of peptides. PCT International Application 2001, WO 01/52898.

36. Achilefu, S. et al. A new method for the synthesis of tri-tert-butyl diethylenetriamine-pentaacetic acid and its derivatives. *Journal of Organic Chemistry* 2000, 65(5), 1562-1565.

37. Muller et al. Eds, *Medical Optical Tomography, SPIE Volume IS*11, 1993.

38. R. B. Dorshow et al. Non-Invasive Fluorescence Detection of Hepatic and Renal Function, *Bull. Am. Phys. Soc.* 1997, 42, 681.

39. R. B. Dorshow et al. Monitoring Physiological Function by Detection of Exogenous Fluorescent Contrast Agents. In *Optical Diagnostics of Biological Fluids IV*, A. Priezzhev and T. Asakura, Editors, Proceedings of SPIE 1999, 3599, 2-8).

40. C. E. Speicher. *The right test: A physician's guide to laboratory medicine*, W. B. Saunders, Philadelphia, Pa., 1989).

What is claimed is:

1. A compound of Formula II, wherein

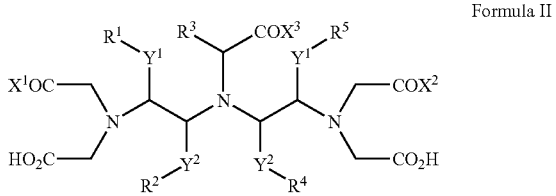

Formula II $X^1$, $X^2$, and $X^3$ are independently selected from $Ar^1$-$Z^1$-, $-O^-$, $-NH(CH_2)_aOH$, $-NH(CH_2)_aCO_2H$, $-NH(CH_2)_aSO_3^-$, $-NH(CH_2)_aOSO_3^-$, $-NH(CH_2)_aNHSO_3^-$, $-O(CH_2)_aSO_3^{-1}$, $-O(CH_2)_aOSO_3^-$, $-O(CH_2)_aNHSO_3^-$, $-NH(CH_2)_aPO_3H^-$, $-NH(CH_2)_aPO_3^=$, $-NH(CH_2)_aOPO_3H^-$, $-NH(CH_2)_aOPO_3^=$, $-NH(CH_2)_aNHPO_3H^-$, $-NH(CH_2)_aNHPO_3^=$, $-O(CH_2)_aPO_3H^-$, $-O(CH_2)_aPO_3$, $-O(CH_2)_aOPO_3H^-$, $-O(CH_2)_aOPO_3^=$, $-O(CH_2)_aNHPO_3H^-$, and $-O(CH_2)_aNHPO_3^=$;

$Y^1$ and $Y^2$ are independently selected from a single bond, $-(CH_2)_m-$, $-(CH_2)_mO-$, $-(CH_2)_mOCO-$, $-(CH_2)_mCO_2-$, $-(CH_2)_mOCNH-$, $-(CH_2)_mOCO_2-$, $-(CH_2)_mNHCO-$, $-(CH_2)_mNHCONH-$, $-(CH_2)_mNHCSNH-$, $-(CH_2)_mOSO_2-$, $-(CH_2)_mOSO_3-$, $-(CH_2)_mSO_2,-$, $-(CH_2)_mNHSO_2,-$ and $-(CH_2)_mSO_2NH-$;

$Z^1$ is $-NH-$, $-O-$, $-NH(CH_2)_m-$, or $-O(CH2)_m-$;

$Ar^1$ is a bicyclic heteroaromatic radical having a base ring structure containing 5 to 10 carbon;

R1 to R5 are independently selected from $Ar^2$-$Z^2$-, hydrogen, C1-C10 alkyl, C1-C10 hydroxyalkyl, C1-C10 polyhydroxyalkyl, carboxyl, C1-C10 carboxyalkyl, C1-C10 alkoxyalkyl, $-(CH_2)_bSO_3^-$, $-(CH_2)_bOSO_3^-$, $-(CH_2)_bNHSO_3^-$, $-(CH_2)_bCO_2(CH_2)_cSO_3^-$, $-(CH_2)_bOCO(CH_2)_cSO_3^-$, $-(CH_2)_bCONH(CH_2)_cSO_3^-$, $-(CH_2)_bNHCO(CH_2)_cSO_3^-$, $-(CH_2)_bNH-$ $CONH(CH_2)_cSO_3^-$, $-(CH_2)_bNHCSNH(CH_2)_cSO_3^-$, $-(CH_2)_bOCONH(CH_2)_cSO_3^-$, $-(CH_2)_bPO_3H^-$, $-(CH_2)_bPO_3^=$, $-(CH_2)_bOPO_3H^-$, $-(CH_2)_bOPO_3^=$, $-(CH_2)_bNHPO_3H^-$, $-(CH_2)_bNHPO_3^=$, $-(CH_2)_bCO_2(CH_2)_cPO_3H^-$, $-(CH_2)_bCO_2(CH_2)_cPO_3^=$, $-(CH_2)_bOCO(CH_2)_cPO_3H^-$, $-(CH_2)_bOCO(CH_2)_cPO_3^=$, $-(CH_2)_bCONH(CH_2)_cPO_3H^-$, $-(CH_2)_bCONH(CH_2)_cPO_3^=$, $-(CH_2)_bNHCO(CH_2)_cPO_3H^-$, $-(CH_2)_bNHCO(CH_2)_cPO_3^=$, $-(CH_2)_bNHCONH(CH_2)_cPO_3H^-$, $-(CH_2)_bNHCONH(CH_2)_cPO_3^=$, $-(CH_2)_bNHCSNH(CH_2)_cPO_3H^-$, $-(CH_2)_bNHCSNH(CH_2)_cPO_3^=$, $-(CH_2)_bOCONH(CH_2)_cPO_3H^-$, or $-(CH_2)_bOCONH(CH_2)_cPO_3^=$;

$Z^2$ is a single bond;

$Ar^2$ is a bicyclic heteroaromatic radical having a base ring structure containing 5 to 10;

a, b, and c independently are 1 to 6; and m is 1 to 10;

with the proviso that at least one of $X^1$ to $X^3$ is $Ar^1$-$Z^1$- or at least one of $R^1$ to $R^5$ is $Ar^2$-$Z_2$-.

2. The compound of claim 1, wherein $X^1$ is $Ar^1$-$Z^1$- and $X^2$ is $-O^-$.

3. The compound of claim 1, wherein each of $X^1$ and $X^2$ is $Ar^1$-$Z^1$-.

4. The compound of claim 2, wherein $Ar^1$ is quinoxaline, quinoxaline carboxylate, or cyanoquinoxaline.

5. The compound of claim 2, wherein $Z^1$- is $-NH-$ or $-NH(CH_2)_m-$.

6. The compound of claim 2, wherein each of $Y^1$ and $Y^2$ is a single bond, $X^3$ is $-O^-$, and each of $R^1$-$R^5$ is hydrogen.

7. The compound of claim 2, wherein $Ar^1$ is quinoxaline, quinoxaline carboxylate, or cyanoquinoxaline; and $Z^1$- is $-NH-$ or $-NH(CH_2)_m-$.

8. The compound of claim 2, wherein $Ar^1$ is quinoxaline, quinoxaline carboxylate or cyanoquinoxaline; each of $Y^1$ and $Y^2$ is a single bond; $X^3$ is $-O^-$; and each of $R^1$-$R^2$ is hydrogen.

9. The compound of claim 2, wherein $Z^1$- is $-NH-$ or $-NH(CH_2)_m-$; each of $Y^1$ and $Y^2$ is a single bond; $X^3$ is $-O^-$; and each of $R^1$-$R^5$ is hydrogen.

10. The compound of claim 2, wherein $Ar^1$ is quinoxaline, quinoxaline carboxylate, or cyanoquinoxaline; $Z^1$- is $-NH-$ or $-NH(CH_2)_m-$; each of $Y^1$ and $Y^2$ is a single bond; $X^3$ is $-O^-$; and each of $R^1$-$R^5$ is hydrogen.

11. The compound of claim 3, wherein $Ar^1$ is quinoxaline, quinoxaline carboxylate, or cyanoquinoxaline.

12. The compound of claim 3, wherein $Z^1$- is $-NH-$ or $-NH(CH_2)_m-$.

13. The compound of claim 3, wherein each of $Y^1$ and $Y^2$ is a single bond; $X^3$ is $-O^-$; and each of $R^1$-$R^5$ is hydrogen.

14. The compound of claim 3, wherein $Ar^1$ is quinoxaline, quinoxaline carboxylate, or cyanoquinoxaline; and $Z^1$- is $-NH-$ or $-NH(CH_2)_m-$.

15. The compound of claim 3, wherein $Ar^1$ is quinoxaline, quinoxaline carboxylate or cyanoquinoxaline; each $Y^1$ and $Y^2$ is a single bond; $X^3$ is $-O^-$; and each of $R^1$-$R^5$ is hydrogen.

16. The compound of claim 3, wherein $Z^1$- is $-NH-$ or $-NH(CH_2)_m-$; each $Y^1$ and $Y^2$ is a single bond; $X^3$ is $-O^-$; and each of $R^1$-$R^5$ is hydrogen.

17. The compound of claim 3, wherein $Ar^1$ is quinoxaline, quinoxaline carboxylate, or cyanoquinoxaline; $Z^1$- is $-NH-$ or $-NH(CH_2)_m-$; each of $Y^1$ and $Y^2$ is a single bond; $X^3$ is $-O^-$; and each of each $R^1$-$R^5$ is hydrogen.

* * * * *

UNITED STATES PATENT AND TRADEMARK OFFICE
CERTIFICATE OF CORRECTION

PATENT NO. : 7,674,902 B2
APPLICATION NO. : 11/572920
DATED : March 9, 2010
INVENTOR(S) : Rajagopalan et al.

It is certified that error appears in the above-identified patent and that said Letters Patent is hereby corrected as shown below:

Column 15

Line 47, "-O(CH$_2$)$_a$PO$_3$" should read -- -O(CH$_2$)$_a$PO$_3^=$ --

Line 57, "or -O(CH2)$_m$" should read -- or -O(CH$_2$)$_m$- --

Line 65, "-(CH$_2$)$_b$OCO(CH$_2$)$_c$SO$_3$-" should read -- -(CH$_2$)$_b$OCO(CH$_2$)$_c$SO$_3^-$ --

Column 16

Line 3, "-(CH$_2$)$_b$OPO$_3^=$" should read -- -(CH$_2$)$_b$OPO$_3^=$ --

Line 7, "(CH$_2$)$_b$CONH" should read -- (CH$_2$)$_b$CONH --

Line 10, "-(CH$_2$)$_b$NHCONH(CH$_2$)$_c$PO$_3^=$" should read -- -(CH$_2$)$_b$NHCONH(CH$_2$)$_c$PO$_3^=$ --

Line 12, "-(CH$_2$)$_b$OCONH(CH$_2$)$_c$PO$_3$H-" should read -- -(CH$_2$)$_b$OCONH(CH$_2$)$_c$PO$_3$H- --

Line 20, "R$^1$ to R$^5$ is Ar$^2$-Z$_2$-" should read -- R$^1$ to R$^5$ is Ar$^2$-Z$^2$- --

Line 36, "R$^1$-R$^2$ is hydro-" should read -- R$^1$-R$^5$ is hydro- --

Signed and Sealed this

Fourth Day of May, 2010

David J. Kappos
*Director of the United States Patent and Trademark Office*